US009206239B2

(12) United States Patent
Cohen

(10) Patent No.: US 9,206,239 B2
(45) Date of Patent: Dec. 8, 2015

(54) TREATMENT OF CANCERS WITH IMMUNOSTIMULATORY HIV TAT DERIVATIVE POLYPEPTIDES

(71) Applicant: PIN Pharma, Inc., New York, NY (US)

(72) Inventor: David I. Cohen, Pelham, NY (US)

(73) Assignee: PIN PHARMA, INC., New York, NY (US)

( * ) Notice: Subject to any disclaimer, the term of this patent is extended or adjusted under 35 U.S.C. 154(b) by 0 days.

(21) Appl. No.: 13/969,917

(22) Filed: Aug. 19, 2013

(65) Prior Publication Data

US 2013/0331335 A1    Dec. 12, 2013

Related U.S. Application Data

(63) Continuation of application No. 12/730,043, filed on Mar. 23, 2010, now Pat. No. 8,530,431.

(60) Provisional application No. 61/162,605, filed on Mar. 23, 2009, provisional application No. 61/306,278, filed on Feb. 19, 2010, provisional application No. 61/310,221, filed on Mar. 3, 2010.

(51) Int. Cl.
*C07K 14/005* (2006.01)
*A61K 31/675* (2006.01)
*A61K 31/7088* (2006.01)

(52) U.S. Cl.
CPC .............. *C07K 14/005* (2013.01); *A61K 31/675* (2013.01); *A61K 31/7088* (2013.01); *C12N 2740/16322* (2013.01)

(58) Field of Classification Search
None
See application file for complete search history.

(56) References Cited

U.S. PATENT DOCUMENTS

| | | | |
|---|---|---|---|
| 5,585,103 A | 12/1996 | Raychaudhuri et al. |
| 5,597,895 A | 1/1997 | Gaynor et al. |
| 5,616,559 A | 4/1997 | Androphy et al. |
| 5,652,122 A | 7/1997 | Frankel et al. |
| 5,656,599 A | 8/1997 | Androphy et al. |
| 5,670,617 A | 9/1997 | Frankel et al. |
| 5,674,980 A | 10/1997 | Frankel et al. |
| 5,686,264 A | 11/1997 | Gaynor et al. |
| 5,747,641 A | 5/1998 | Frankel et al. |
| 5,804,604 A | 9/1998 | Frankel et al. |
| 5,817,308 A | 10/1998 | Scot et al. |
| 5,889,175 A | 3/1999 | Mehtali et al. |
| 5,891,994 A | 4/1999 | Goldstein |
| 5,942,401 A | 8/1999 | Van Baalen et al. |
| 5,981,258 A | 11/1999 | Mehtali et al. |
| 6,024,965 A | 2/2000 | Van Baalen et al. |
| 6,132,721 A | 10/2000 | Zagury et al. |
| 6,193,981 B1 | 2/2001 | Goldstein |
| 6,194,388 B1 | 2/2001 | Krieg et al. |
| 6,200,575 B1 | 3/2001 | Zagury et al. |
| 6,207,646 B1 | 3/2001 | Krieg et al. |
| 6,228,369 B1 | 5/2001 | Mehtali et al. |
| 6,239,116 B1 | 5/2001 | Krieg et al. |
| 6,270,769 B1 | 8/2001 | Raychaudhuri et al. |
| 6,284,252 B1 | 9/2001 | Mehtali et al. |
| 6,316,003 B1 | 11/2001 | Frankel et al. |
| 6,319,666 B1 | 11/2001 | Van Baalen et al. |
| 6,339,068 B1 | 1/2002 | Krieg et al. |
| 6,406,705 B1 | 6/2002 | Davis et al. |
| 6,420,141 B1 | 7/2002 | Zagury et al. |
| 6,495,347 B1 | 12/2002 | Mizzen et al. |
| 6,497,880 B1 | 12/2002 | Wisniewski |
| 6,524,582 B2 | 2/2003 | Goldstein |
| 6,524,825 B1 | 2/2003 | Mizzen et al. |
| 6,525,179 B1 | 2/2003 | Goldstein |
| 6,593,292 B1 | 7/2003 | Rothbard et al. |
| 6,657,055 B2 | 12/2003 | Siegel et al. |
| 6,667,151 B1 | 12/2003 | Cohen |
| 6,686,333 B1 | 2/2004 | Kashanchiet et al. |
| 6,797,491 B2 | 9/2004 | Neefe et al. |
| 7,087,377 B2 | 8/2006 | Loret |
| 8,530,431 B2 | 9/2013 | Cohen |
| 2002/0091073 A1 | 7/2002 | Finkel et al. |
| 2002/0193330 A1 | 12/2002 | Hone et al. |
| 2002/0197269 A1 | 12/2002 | Lingnau et al. |
| 2003/0003160 A1 | 1/2003 | Zagury et al. |
| 2003/0091599 A1 | 5/2003 | Davis et al. |
| 2003/0099663 A1 | 5/2003 | Fleitmann et al. |
| 2003/0099664 A1 | 5/2003 | Wisniewski |

(Continued)

FOREIGN PATENT DOCUMENTS

EP        614980        9/1994
EP        673948        11/1998

(Continued)

OTHER PUBLICATIONS

Chenciner et al., Enhancement of humoral immunity to SIVenv following simultaneous inoculation of mice by three recombinant adenoviruses encoding SIVenv/poliovirus chimeras, Tat and Rev. AIDS Res. and Hum. Retroviruses 13: 801-806 (1997).
Cho et al., In virto induction of carcioembryonic antigen (CEA)-specific cytotoxic T lymphocytes by dendritic cells transduced with recombinant adenoviruses. Vaccine, vol. 22, pp. 224-236 (2003).
Cohen et al., Pronounced acute immunosuppression in vivo mediated by HIV-1 Tat challenge. Proc. Natl. Acad. Sci. USA, 96(19): 10842-10847 (1999).
Dalgleish et al., Cancer vaccines as a therapeutic modality: the long trek. Cancer Immunol. Immunother., 55: 1025-1032 (2006).
Dalyot-Herman et al., Reversal of CD8+ T cell ignorance and induction of anti-tumor immunity by peptide-pulsed APC. J. Immunol., 165: 6731-7 (2000).
Durrant et al., Cancer vaccines entering Phase III clinical trials. Expert Opinion Emerging Drugs, vol. 8, No. 2, pp. 489-500 (2003).

(Continued)

*Primary Examiner* — Karlheinz R Skowronek
*Assistant Examiner* — Lianko Garyu
(74) *Attorney, Agent, or Firm* — K&L Gates LLP; Louis C. Cullman; Michelle Glasky Bergman

(57) ABSTRACT

Disclosed herein are methods of treating cancer by administering a modified Human Immunodeficiency Virus (HIV) trans-activator of transcription (Tat) polypeptide with increased immunostimulatory properties relative to the non-modified Tat polypeptide.

19 Claims, 12 Drawing Sheets

(56) References Cited

U.S. PATENT DOCUMENTS

| | | | |
|---|---|---|---|
| 2003/0148456 | A1 | 8/2003 | Mizzen et al. |
| 2003/0158134 | A1 | 8/2003 | Voss |
| 2003/0162719 | A1 | 8/2003 | Rothbard et al. |
| 2003/0166832 | A1 | 9/2003 | Goldstein |
| 2003/0180326 | A1 | 9/2003 | Goldstein |
| 2003/0190326 | A1 | 10/2003 | Dalenccon et al. |
| 2003/0194408 | A1 | 10/2003 | Goldstein |
| 2003/0215797 | A1 | 11/2003 | Cohen |
| 2003/0224010 | A1 | 12/2003 | Davis et al. |
| 2003/0232074 | A1 | 12/2003 | Lipford et al. |
| 2004/0001852 | A1 | 1/2004 | Zagury et al. |
| 2004/0005330 | A1 | 1/2004 | Rappaport et al. |
| 2004/0009949 | A1 | 1/2004 | Krieg et al. |
| 2004/0028652 | A1 | 2/2004 | Wang et al. |
| 2004/0034209 | A1 | 2/2004 | Ho et al. |
| 2004/0054137 | A1 | 3/2004 | Thomson et al. |
| 2005/0022690 | A1 | 2/2005 | Peach et al. |
| 2005/0244434 | A1 | 11/2005 | Cohen |
| 2007/0248618 | A1 | 10/2007 | Cohen |
| 2008/0044435 | A1 | 2/2008 | Cohen |
| 2009/0181045 | A1 | 7/2009 | Cohen |
| 2009/0202585 | A1 | 8/2009 | Cohen |
| 2012/0093858 | A1 | 4/2012 | Cohen |
| 2012/0121636 | A1 | 5/2012 | Cohen |

FOREIGN PATENT DOCUMENTS

| | | |
|---|---|---|
| EP | 814834 | 9/2000 |
| EP | 1279404 | 1/2003 |
| FR | 2631355 | 9/1996 |
| WO | 91/15224 | 10/1991 |
| WO | 91/18454 | 11/1991 |
| WO | 94/15634 | 7/1994 |
| WO | 95/31999 | 11/1995 |
| WO | 96/27389 | 9/1996 |
| WO | 98/14589 | 4/1998 |
| WO | 98/17309 | 4/1998 |
| WO | 98/43669 | 10/1998 |
| WO | 98/46083 | 10/1998 |
| WO | 99/02185 | 1/1999 |
| WO | 99/16884 | 4/1999 |
| WO | 99/27958 | 6/1999 |
| WO | 99/33346 | 7/1999 |
| WO | 99/33872 | 7/1999 |
| WO | 00/03732 | 1/2000 |
| WO | 00/59935 | 10/2000 |
| WO | 00/78969 | 12/2000 |
| WO | 01/00232 | 1/2001 |
| WO | 01/24822 | 4/2001 |
| WO | 01/43771 | 6/2001 |
| WO | 01/78775 | 10/2001 |
| WO | 02/085938 A1 | 10/2002 |
| WO | 03/035097 A1 | 5/2003 |
| WO | 2004/108753 | 12/2004 |
| WO | 2005/030799 | 4/2005 |
| WO | 2005/049093 A1 | 6/2005 |
| WO | 2005/090392 | 9/2005 |
| WO | 2005/097179 | 10/2005 |
| WO | 2005/097180 A1 | 10/2005 |
| WO | 2006/033665 | 3/2006 |

OTHER PUBLICATIONS

Fanales-Belasio et al., Naïve HIV-1 Tat protein targets monocyte-derived dendritic cells and enchances their maturation, function, and antigen-specific T cell responses. J. Immunol., 168: 197-206 (2002).
Fawell et al., Tat-mediated delivery of heterologuos proteins into cells. Proc. Natl. Acad. Sci., vol. 91, pp. 664-668 (1994).
Firfer, Database [Online], New HIV vaccine concept may extend hope to those already infected, http://cnn.com/Health/Aids/9908/29/aids.vaccine (1999).
Fisher et al., Dominant interfering Fas gene mutations impair apoptosis in a human autoimmune lymphoproliferative syndrome. Cell, vol. 81, pp. 935-946 (1995).
Follen et al., Cervical cancer chemoprevention, vaccines, and surrogate endpoint biomarkers. American Cancer Society, Cancer Supplement, vol. 98, No. 9, pp. 2044-2051 (2003).
Frankel et al., Activity of synthetic peptides from the TAT protein of human immunodeficiency virus type 1. Proc. Natl. Acad. Sci., vol. 86, pp. 7397-7401 (1989).
Frankel et al., Cellular uptake of the Tat protein from human immunodeficiency virus. Cell, 55: 1189-93 (1988).
Friedman et al., Expression of a truncated viral trans-activator selectively impedes lytic infection by its cognate virus. Nature, vol. 335, pp. 452-454 (1988).
Fultz et al. "SIVsmm Infection of Macaque and Mangabey Monkeys: Correlation between in vivo and in vitro properties of different isolates." Develop. biol. Standard., vol. 72, pp. 253-258, 1990.
Gallo, RC., Tat as one key HIV-induced immune pathogenesis and Tat toxoid as an important component of a vaccine. Proc. Natl. Acad. Sci. USA, vol. 96, pp. 8324-8326 (1999).
Giannouli et al., Fusion of a tumour-associated antigen to HIV-1 Tat improves protein-based immunotherapy of cancer. Anticancer Research, vol. 23, No. 4, pp. 3523-3532 (2003).
Goldstein, G., HIV-1 Tat protein as a potential AIDS vaccine. Nature Medicine, vol. 1, No. 9, pp. 960-964 (1996).
Gringeri et al., Safety and immunogenicity of HIV-1 Tat toxoid in immunocompromised HIV-1-infected patients. Journal of Human Virology, vol. 1, No. 4, pp. 293-298 (1998).
Gringeri et al., Tat toxoid as a component of a preventive vaccine in seronegative subjects. Journal of Acquired Immune Deficiency Syndromes and Human Retrovirology, vol. 20, No. 4, pp. 371-375 (1999).
Harrop et al., Recombinant viral vectors: cancer vaccines. Adv. Drug Delivery Rev., 58: 931-947 (2006).
Heneine et al., Stepwise iodination. A general procedure for detoxification of proteins suitable for vaccine development and antiserum production. Biologicals 26, 25-32 (1998).
Hernando et al., Dendritic cell-based vaccines in breast and gynaecologic cancer. Anticancer Res., 23: 4293-4304 (2003).
Hsieh et al., Tumor-induced immunosupression: a barrier to immunotherapy of large tumors by cytokine-secreting tumor vaccine. Human Gene Therapy, vol. 11, pp. 681-692 (2000).
International Search Report for international application PCT/US2005/008519 filed on Mar. 16, 2005.
International Search Report for international application PCT/US2005/008634 filed on Mar. 16, 2005.
Ishigami et al., Tumor-associated macrophage (TAM) infiltration in gastric cancer. Anticancer Res., vol. 23, pp. 4079-4084 (2003).
Jager et al., Identification of tumor antigens as potential target antigens for immunotherapy by serological expression cloning, http://www.springerlink.com/media/gmgkwgmxxeebf3wn9h2m/Contributins/X/3/9/F/X39, pp. 1-9 (2004).
Jasinska et al., Inhibition of tumor cell growth by antibodies induced after vaccination with peptides derived from the extracellular domin of Her-2/NEU. Int. J. Cacner, vol. 107, pp. 976-983 (2003).
Jiang et al., Fas mediates apoptosis and oxidant-induced cell death in cultured hRPE cells. Invest Ophthalmol. Vis. Sci., vol. 42, No. 3, pp. 645-655 (2000).
Kanazawa et al., Effect of DC therapy combined with chemotherapy in advanced cancer cases. Jpn J. Cancer Chemother., vol. 30, No. 11, pp. 1655-1660 (2003).
Kjaergaard et al., Electrofusion of syngeneic dendritic cells and tumor generates potent therapeutic vaccine. Cellular Immunology, vol. 225, pp. 65-74 (2003).
Kuppuswamy et al., Multiple functional domains of Tat, the trans-activator of HIV-1, defined by mutational analysis. Nucleic Acids Research, vol. 17, No. 9, pp. 3551-3561 (1989).
Lane et al. "The expression and prognostic value of the guanine nucleotide exchange factors (GEFs) Trio, Vay1 and TIAM-1 in human breast cancer." BioMed Central, Oct. 2008.
Leonard et al., Periodate oxidation of sulfides to sulfoxides. Scope of the Reaction, the Journal of Organic Chemistry, vol. 27, No. 1, pp. 282-284 (1962).
Lepple-Wienhues et al., Stimulation of CD95 (FAs) blocks T lymphocyte calcium channels through sphingomyelinase and sphingolipids. PNAS, vol. 96, No. 24, pp. 13795-13800 (1999).

(56) References Cited

OTHER PUBLICATIONS

Li et al., Induction of apoptosis in uninfected lymphocytes by HIV-1 Tat protein. Science, vol. 268, pp. 429-431 (1995).
Li et al., Tat protein induces self-perpetuating permissivity for productive HIV-1 infection. PNAS, vol. 94, pp. 8116-8120 (1997).
Lin et al., the macrophage growth factor CSF-1 in mammary gland development and tumor progression. Journal of Mammary Gland Biology and Neoplasia, vol. 7, No. 2, pp. 147-162 (2002).
Liu et al., Concurrent delivery of tumor antigens an activation signals to dendritic cells by irradiated CD40 ligand-transfected tumor cells resulted in efficient activation of specific CD8+ T cells . Cancer Gene Therapy , vol. 11, pp. 135-147 (2004).
Martin et al., Human embryonic stem cells express an immunogenic nonhuman sialic acid. Nat. Med. 11: 228-232 (2005).
Medina et al., Regulatory role of CD95 ligation on human B cells induced in vivo capable of spontaneous and high-rate Ig secretion. Eur. J. Immunol., vol. 27, pp. 700-706 (1997).
Moy et al., Tat-mediated protein delivery can facilitate MHC class I presentation of antigens. Mol. Biotechnol. 6: 105-113 (1996).
Nagata S., Apoptosis by death factor. Cell, vol. 88, pp. 355-365 (1997).
Niesner et al., Quantitation of the tumor-targeting properties of antibody fragments conjugated to cell-permeating HIV-1 Tat peptdies. Bioconj. Chem. 13: 729-736 (2002).
Nouri-Shirazi et al., Dendritic cell based tumor vaccines. Immunology Letters, vol. 74, pp. 5-10 (2000).
Novak et al., Engagement of FceRl on human monocytes induces the production of IL-10 and prevent their differentiation in dendritic cells. J. Immunol., 167: 797-804 (2001).
Darbinian et al., Growth inhibition of glioblastoma cells by human pur alpha. Journal of Cellular Physiology, vol. 189, No. 3, pp. 334-340 (2001).
Park et al., Mutations in both gp120 and gp41 are responsible for the broad neutralization resistance of variant human immunodeficiency virus type 1 MN to antibodies directed at V3 and non-V3 epitopes. Journal of Virology, vol. 72, No. 9, pp. 7099-7107 (1998).
Peter et al., Resistance of cultured peripheral T cells towards activation-induced cell death involves a lack of recruitment of FLICE (MACH/caspase 8) to the CD95 death-inducing signaling complex. Eur. J. Immunol., vol. 27, pp. 1207-1212 (1997).
Phan et al., Cancer regression and autoimmunity induced by cytotoxic T lymphocyte-associated antigen 4 blockade in patients with metastatic melanoma. PNAS, 100: 8372-7 (2003).
Prive et al. "Specific peptides for the therapeutic targeting of oncogenes." Current Opinion in Genetics & Development, 2006, 16:71-77.
Quinones-Mateu et al., LATR and tat variability of HIV-1 isolates from patients with divergent rates of disease progression. Virus Research, 57, 11-20 (1998).
Rana et al., Biochemical and functional interactions between Hiv-1 Tat protein and TAR RNA. Archives of Biochemistry and Biophysics, vol. 365, No. 2, pp. 175-185 (1999).
Re et al., Effect of antibody to HIV-1 Tat protein on viral replication in vitro and progression of HIV-1 disease in vivo. Journal of Acquired immune deficiency syndromes and human retrovirology, 10, 408-416 (1995).
Reinhold et al., HIV-1 Tat: immunosuppression via TFG-beta1 induction. Immunology Today, 20(8): 384 (1999).
Riffkin et al., A single amino-acid change between the antigenically different extracellular erine proteases V2 and B2 from Dichelobacter nodosus. Gene, vol. 167, pp. 279-283 (1995).
Schluesener HJ, Protection against experimental nervous system autoimmune diseases by a human immunodeficiency virus-1 Tat peptide-based polyvalent vaccine. J. Neurosci. Res. 46:258-262 (1996).
Schwarze et al., In vivo protein transduction: delivery of a biologically active protein into the mouse. Science 285: 1569-1572 (1999).
Small et al., Immunotherapy of hormone-refractory prostate cancer with antigen-loaded dendritic cells. Journal of Clinical Oncology, vol. 18, No. 23, pp. 3894-3903 (2000).

Waldmann, T.A., Immunotherapy: past, present and future. Nat. Med. 9(3): 269-277 (2003).
Wang et al., Induction of CD4+ T-cell dependent antitumor immunity by TAT-mediated tumor antigen delivery into dendritic cells. J. Clin. Invest., vol. 109, No. 11, pp. 1463-1470 (2002).
Zhang et al., Induction of specific T cell tolerance by Fas ligand-expressing antigen-presenting cells. J. Immunol., 162: 1423-1430 (1999).
Tasca et al., Escpate of monocyte-derived dendritic cells of HIV-1 infected individuals from natural killer cell-mediated lysis. AIDS, vol. 17, pp. 2291-2298 (2003).
Tosi et al., Highly stable oligomerization forms of HIV-1 Tat detected by monoclonal antibodies and requirement of monomeric forms for the transactivating function on the HIV-1 LTR. Eu.r. J. Immunol., 30: 1120-1126 (2000).
Turtle et al., Dendritic cells cells in tumor immunology and immunotherapy. Current Drug Targets, vol. 5, No. 1, pp. 17-39 (2004).
Viscidi et al., Inhibition of antigen-induced lymphocyte proliferation by Tat protein from HIV-1. Science, 246: 1606-1608 (1989).
Visscher et al., Clinicopathologic analysis of macrophage infiltrates in breast carcinoma. Path. Res. Pract. (Suppl.), vol. 191, pp. 1133-1139 (1995).
Vocero-Akbani et al., Killing HIV-infected cells by transduction with an HIV protease-activated caspase-3 protein. Nature Medicine, vol. 5, No. 1, pp. 29-33 (1999).
Von Bernstorff et al., Systemic and local immunosupression in pancreatic cancer patients. Clinical Cancer Research, vol. 7, Supplement, pp. 925s-932s (2001).
Wachsman et al., HTLV x Gene mutants exhibit novel transcriptional regulatory phenotypes. Science, vol. 235, pp. 674-677 (1987).
Wadia et al., Transmembrane delivery of protein and peptide drugs by TAT-mediated transduction in the treatment of cancer. Advanced Drug Delivery Reviews 57, 579-596 (2005).
Database UniPort [online] RecName: Full=Protein Tat; AltName: Full=Transactivating regulatory protein. Accession No. P27975. Aug. 1, 1992 (Query: SA977698.3).
Paillard F. Immunosuppression mediated by tumor cells: a challenge for immunotherapeutic approaches. Hum Gene Ther. Mar. 20, 2000;11(5):657-8.
Agwale et al., A Tat subunit vaccine confers protective immunity against the immune-modulating activity of the human immunodeficiency virus type-1 Tat protein in mice. PNAS, 99: 10037-10041 (2002).
Arlen et al., Strategies for the development of PSA-based vaccines for the treatment of advanced prostate cancer. Expert Rev. Vaccines, vol. 2, No. 4 , pp. 483-493 (2003).
Augustine, R.L., Oxidation techniques and applications in organic synthesis, vol. 1, pp. 244-248 (1969).
Baghian et al., Protective immunity against lethal HSV-1 challenge in mice by nucleic acid-based immunization with herpes simplex virus type-1 genes specifying glycoproteins gB and gD. J. Med. Microbiol., vol. 51, pp. 350-357 (2002).
Banchereau et al., Dendritic cells as vectors for therapy. Cell, 106: 271-274 (2001).
Bayer et al., Structural studies of HIV-1 Tat protein. J. Mol. Biol., vol. 247, pp. 529-535 (1995).
Beissert e al., IL-10 inhibits tumor antigen presentation by epidermal antigen-presenting cells. The Journal of Immunology, vol. 154, pp. 1280-1286 (1995).
Bettelli et al., Th-17 cells in the inner circle of immunity and autoimmunity. Nat. immunol., 8(4): 345-350 (2007).
Boykins et al., Immunization with a novel HIV-1-Tat multiple-peptide conjugate induces effective immune response in mice. Peptides, vol. 21, No. 12, pp. 1839-1847 (2000).
Badley et al., Macrophage dependent apoptosis of CD4+ T lymphocytes from HIV-infected individuals is mediated by FasL and tumor necrosis factor. J. Exp. Med., vol. 185, No. 1, pp. 55-64 (1997).
Badley et al., Upregulation of Fas ligand expression by human immunodeficiency virus in human macrophages mediates apoptosis of uninfected T lymphocytes. J. Virol., 70(1): 199-206 (1996).

(56) References Cited

OTHER PUBLICATIONS

Le Buanec et al., A prophylactic and therapeutics AIDS vaccine containing as a component the innocuous Tat Toxoid. Biomedicine and Pharmacotheraphy, vol. 52, No. 10, pp. 431-435 (1998).

Caputo et al., Immunization with low doses of HIV-1 Tat DNA delivered by novel cationic block copolymers induces CTL responses against Tat. Vaccine, vol. 21, pp, 1103-1111 (2003).

Caselli et al., DNA immunization with HIV-1 Tat DNA mutated in the trans activation domain induces humoral and cellular immune responses against wild-type Tat. J. Immunol., 162: 5631-5638 (1999).

Cataro et al., Control of Shiv-89.6P-Infection of cynomolgus monkeys by HIV-1 tat protein vaccine. Nature Medicine, 5(16), 643-650 (1999).

Chang et al., HIV-1 Tat protein exits from cells via a leaderless secretory pathway and binds to extracellular matrix-associated heparan sulfate proteoglycans through its basic region. AIDS, vol. 11, No. 12, p. 1421-1431 (1997).

Cheadle et al., Identification of a Src SH3 domain binding motif by screening a random phage display library. The Journal of Biological Chemistry, vol. 269, No. 39, pp. 24034-24039 (1994).

SEQUENCE LISTING

<160> NUMBER OF SEQ ID NOS: 4

<210> SEQ ID NO 1
<211> LENGTH: 101
<212> TYPE: PRT
<213> ORGANISM: Human immunodeficiency virus

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Lys Lys Ala Leu Gly Ile Ser Tyr Gly
        35                  40                  45

Arg Lys Lys Arg Arg Gln Arg Arg Ala Pro Glu Asp Ser Gln Thr
    50                  55                  60

His Gln Val Ser Pro Pro Lys Gln Pro Ala Pro Gln Phe Arg Gly Asp
 65                  70                  75                  80

Pro Thr Gly Pro Lys Glu Ser Lys Lys Lys Val Glu Arg Glu Thr Glu
                 85                  90                  95

Thr His Pro Val Asp
            100

<210> SEQ ID NO 2
<211> LENGTH: 102
<212> TYPE: PRT
<213> ORGANISM: Artificial Sequence
<220> FEATURE:
<223> OTHER INFORMATION: Nani-P1 modified HIV Tat sequence

<400> SEQUENCE: 2

Met Glu Pro Val Asp Ala Asn Leu Glu Ala Trp Lys His Ala Gly Ser
 1               5                  10                  15

Gln Pro Arg Lys Thr Ala Cys Thr Thr Cys Tyr Cys Lys Lys Cys Cys
                20                  25                  30

Phe His Cys Gln Val Cys Phe Thr Arg Lys Gly Leu Gly Ile Ser Tyr
             35                  40                  45

Gly Arg Lys Lys Arg Arg Gln Arg Arg Ala Pro Gln Asp Ser Gln
 50                  55                  60

Thr His Gln Ala Ser Leu Ser Lys Gln Pro Ala Ser Gln Ser Arg Gly
 65                  70                  75                  80

Asp Pro Thr Gly Pro Thr Glu Ser Lys Lys Lys Val Glu Arg Glu Thr
                 85                  90                  95

Glu Thr Asp Pro Phe Asp
            100

<210> SEQ ID NO 3
<211> LENGTH: 119
<212> TYPE: PRT
<213> ORGANISM: Artificial Sequence
<220> FEATURE:
<223> OTHER INFORMATION: Nani-P2 modified HIV Tat sequence

<400> SEQUENCE: 3

Met Asp Pro Lys Gly Glu Glu Asp Gln Asp Val Ser His Gln Asp Leu
 1               5                  10                  15

Ile Lys Gln Tyr Arg Lys Pro Arg Thr Ala Cys Asn Asn Cys Tyr Cys
                20                  25                  30

Lys Lys Cys Cys Phe His Cys Tyr Ala Cys Phe Leu Arg Lys Gly Leu
             35                  40                  45

Gly Ile Thr Tyr His Ala Phe Arg Thr Arg Arg Lys Lys Ile Ala Ser
 50                  55                  60

Ala Asp Arg Ile Pro Val Pro Gln Gln Ser Ile Ser Ile Arg Gly Arg
 65                  70                  75                  80

Asp Ser Gln Thr Thr Gln Glu Ser Gln Lys Lys Val Glu Glu Gln Ala
                 85                  90                  95

Lys Ala Asn Leu Arg Ile Ser Arg Lys Asn Leu Gly Asp Glu Thr Arg
                100                 105                 110

Gly Pro Val Gly Ala Gly Asn
            115

<210> SEQ ID NO 4
<211> LENGTH: 130
<212> TYPE: PRT
<213> ORGANISM: Artificial Sequence -continued

```
<220> FEATURE:
<223> OTHER INFORMATION: Nani-P3 modified HIV Tat sequence

<400> SEQUENCE: 4

Met Glu Thr Pro Leu Lys Glu Gln Glu Asn Ser Leu Glu Ser Cys Arg
1               5                   10                  15

Glu His Ser Ser Ser Ile Ser Glu Val Asp Val Pro Thr Pro Val Ser
                20                  25                  30

Cys Leu Arg Lys Gly Gly Arg Cys Trp Asn Arg Cys Ile Gly Asn Thr
            35                  40                  45

Arg Gln Ile Gly Ser Cys Gly Val Pro Phe Leu Lys Cys Cys Lys Arg
        50                  55                  60

Lys Pro Phe Thr Arg Lys Gly Leu Gly Ile Ser Tyr Gly Arg Lys Lys
65                  70                  75                  80

Arg Arg Gln Arg Arg Arg Ala Pro Gln Asp Ser Gln Thr His Gln Ala
                85                  90                  95

Ser Leu Ser Lys Gln Pro Ala Ser Gln Ser Arg Gly Asp Pro Thr Gly
            100                 105                 110

Pro Thr Glu Ser Lys Lys Lys Val Glu Arg Glu Thr Glu Thr Asp Pro
        115                 120                 125

Phe Asp
    130
```

TREATMENT OF CANCERS WITH IMMUNOSTIMULATORY HIV TAT DERIVATIVE POLYPEPTIDES

CROSS-REFERENCE TO RELATED APPLICATIONS

The present application is a continuation of U.S. patent application Ser. No. 12/730,043 filed Mar. 23, 2010, which claims the benefit under 35 USC §119(e) to U.S. Provisional Patent Applications 61/162,605 filed Mar. 23, 2009, 61/306,278 filed Feb. 19, 2010 and 61/310,221 filed Mar. 3, 2010. The entire contents of each of these applications are incorporated by reference herein.

FIELD OF THE INVENTION

The present invention relates to the field of immune-based therapeutic agents for cancer.

BACKGROUND

The Human Immunodeficiency Virus (HIV) trans-activator of transcription (Tat) is a variable RNA binding peptide of 86 to 110 amino acids in length that is encoded on two separate exons of the HIV genome. Tat is highly conserved among all human lentiviruses and is essential for viral replication. When lentivirus Tat binds to the TAR (trans-activation responsive) RNA region, transcription (conversion of viral RNA to DNA then to messenger RNA) levels increase significantly. It has been demonstrated that Tat increases viral RNA transcription and it has been proposed that Tat may initiate apoptosis (programmed cell death) in T4 cells and macrophages (a key part of the body's immune surveillance system for HIV infection) and possibly stimulates the over production of alpha interferon ($\alpha$-interferon is a well established immunosuppressive cytokine).

Extracellular Tat's presence early in the course of HIV infection could reduce a patient's immune response, giving the virus an advantage over the host. Furthermore, the direct destruction of T4 cells and induction of $\alpha$-anterferon production could help explain the lack of a robust cellular immune response seen in Acquired Immunodeficiency Syndrome (AIDS) patients, as well as accounting for the initial profound immunosuppression.

However, Tat protein isolated from HIV-infected long term non-progressors (LTNP) is different from C-Tat found in AIDS patents. The Tat protein found in LTNP is capable of trans-activating viral RNA, however, LTNP Tat (designated herein after as IS-Tat for immunostimulatory Tat) does not induce apoptosis in T4 cells or macrophages and is not immunosuppressive. Moreover, T4 cells infected ex vivo with HIV isolated from LTNP (such cell lines are designated Tat TcL) can result in the over expression of IS-Tat proteins, often to the virtual exclusion of other viral proteins, that are strongly growth promoting rather than pro-apoptotic. The Tat genes cloned from these Tat TcLs reveal sequence variations in two Tat regions, at the amino terminus and within the first part of the second exon. These surprising discoveries could help explain why HIV infected LTNP T4 cells do not die off at the staggering rate seen in HIV infected individuals that progress to AIDS.

Additionally, variants of Tat are found in lentiviruses which infect monkey species yet do not result in the development of immunodeficiency and epidemic infection. These variant Tat proteins direct monocyte differentiation into dendritic cells (DCs) which stimulate cytotoxic T lymphocyte (CTL) responses. These simian Tat variants, and other Tat variants that are not immunosuppressive, have been termed attenuated or immunostimulatory Tat (IS-Tat).

Based on observations with long-term CD4+ Tat T cell lines, clinical observations, and experiments in animals, attenuated Tat (more specifically IS-Tat or, alternatively, Tat proteins that have been chemically or physically altered) may act as an immune stimulant activating T4 cells inducing their proliferation. This principle may help to explain the stable T4 levels seen in LTNP. Moreover, attenuated Tat may be useful as an adjuvant when co-administered with other active vaccine components such as, but not limited to, vaccines for other viruses, bacteria, rickettsia and cancer cells.

Cancers and chronic infections are the most prominent examples of common human diseases that respond to immune-based treatments. Although infections were the first diseases to be controlled by immunization, clinical trials in humans have established that an immune response, particularly of the CTL arm of the immune system, could regress some human melanomas and renal cancers. These observations were broadened by the discovery that DCs, a specific class of antigen-presenting cells (APC), are particularly effective at initiating CTL activity against cancers and other diseases. Technologies that target and activate DC have yielded some early successes against human cervical pre-malignancies, caused by infection with Human Papilloma Virus (HPV) and human lung cancer. In contrast to chemotherapeutic drugs currently used against cancer, agents that provoke a CTL response against cancer potentially are accompanied by few side effects, owing to the great specificity of the immune response.

Efforts to develop immunotherapeutic drugs that treat cancer have been hampered by technical difficulties in targeting and activating DC to deliver and sustain the required entry signals to the CTL. Antigen targeting for the induction of a CTL response is a challenge insofar as natural processing requires that the antigen enter the cytoplasm of the cell in order to bind to the immune system's major histocompatibility complex (MHC) Class I antigen, a prerequisite to CTL activation because the ligand for activating the T cell receptor on CTL is a complex of antigen and MHC Class I. In almost all cases, protein antigens, even when they are coupled with a DC co-activator, enter exclusively into the alternative MHC Class II antigen presentation pathway that excludes CTL stimulation. This can be overcome, in part, by peptide-based technologies, because peptides bind to MHC Class I that is already on the surface of the DC. However, this technology is non-specific and most peptides are poor DC activators, which limits their efficacy as human treatments for cancer.

A limited group of biological proteins are known to stimulate a CTL response. Variants and derivatives of the Human Immunodeficiency Virus 1 (HIV-1) trans-activator of transcription (Tat) can stimulate this CTL response. Additional biologics that are currently known to directly trigger a CTL response are based on heat shock proteins (HSP), or on the outer coat protein of certain bacteria. Heat shock proteins have shown limited efficacy in the treatment of certain genital neoplasms related to HPV infection.

Breast cancer is a leading cause of cancer-related deaths in women worldwide. Approximately 1 million new breast cancer cases occur annually resulting in 370,000 deaths around the world. More than 200,000 new cases of invasive breast cancer are diagnosed in the US each year, with approximately 45,000 deaths attributed to this disease making breast cancer the second leading cause of cancer mortality in the U.S. among women, and the fifth leading cause of cancer deaths overall. After a steady decline in morbidity from breast cancer, mean breast cancer survival from time of diagnosis of widely-invasive (Stage 4) disease has not changed over the last two decades. The five year survival rate for stage 4 breast cancer has remained at about 20% since 1988 meaning that the survival advantages of the newer agents have run their course by end stage disease.

Treatment of breast cancer in the adjuvant setting experienced significant improvements over the last forty years. In addition to better tumorectomy, radiotherapy, standard chemotherapy and hormone replacement therapy, new classes of therapies emerged with distinct oncolytic mechanisms, such as TAXOL® (paclitaxel) and HERCEPTIN® (trastuzumab). HERCEPTIN® was the last of these agents to be introduced in 2003. It has not significantly expanded in patient reach since 2007. Additionally HERCEPTIN® efficacy is limited to only 20% of women with breast cancer, those who overexpress the Her2/neu oncogene most prominently. Thus, new and more obliterative agents are needed to combat and prevent breast cancer.

Under investigation to improve management of many cancers, immunotherapy is one targeted mechanism that could control tumor growth and prevent metastases while avoiding many of the side effects associated with standard therapies. This latter consideration is particularly important insofar as breast cancer is a disease that disproportionately affects younger women of childbearing age. Early breast cancer immunotherapy research focused on ways to target the natural immune response against cancer cells by administering either a vaccine or monoclonal antibody for a breast cancer antigen. While this approach made good sense owing to breast cancer being a rich source of tumor-specific proteins (e.g. the lactation-antigens mammaglobin A and lactadherin among others) it proved largely unsuccessful because antibody, in contrast to cytolytic T cell activation, appears to have limited utility for controlling solid tumor growth under most settings.

Next generation breast cancer immunotherapies have focused on ways to enhance the pre-existing anti-breast cancer immune response of the patient based on the theory that immune suppression also limited the efficacy of tumor-targeting strategies. One such immunotherapeutic is a monoclonal antibody directed against CTLA4, a receptor on cytolytic T cells implicated in suppression. While demonstrating some promise against melanoma and ovarian cancer, anti-CTLA4 has proven ineffective as a stand-alone agent in animal models of breast cancer including those employed in the studies reported here. A second class of immunostimulants evaluated in cancers, the toll-like receptor (TLR) agonists, work by initiating new triggering signals into the immune system from monocyte-derived dendritic cells. These agents to date have demonstrated limited utility in most solid cancers including breast cancer, in part because they rapidly induce immunosuppression concomitant to T cell activation.

Human Immunodeficiency Virus infection initiates a progressive immunosuppression that, absent treatment, routinely progresses to AIDS and thereafter death of the infected individual. As immunosuppression is implicated in various models of solid cancer progression, including breast cancer, it is not surprising that HIV-infected persons are at increased risk for various malignancies, specifically non-Hodgkin lymphoma (NHL), Kaposi sarcoma (KS) and invasive cervical cancer, which are AIDS-defining cancers in HIV-infected individuals. Paradoxically, at least three groups have reported a decreased risk for invasive breast cancer in women with progressive HIV disease. HIV-infected women have a statistically significant pattern of decreasing relative risk (RR) for breast cancer when compared with the French general population. Following an AIDS epidemic in Tanzania, a second group found a statistically significant decrease in the incidence of breast cancer, in both men and women. Thirdly, a US consortium analyzing over 8500 cases of progressive HIV disease reported a statistically significant decreased risk ($p<0.05$) in the development of breast cancer that reverted to baseline once control of viral replication was achieved.

SUMMARY OF THE INVENTION

Disclosed herein are derivatives of the Human Immunodeficiency Virus (HIV) trans-activator of transcription (Tat) protein for use as cancer immunotherapeutic agents.

In one embodiment, a pharmaceutical composition is provided comprising a modified amino acid sequence of Human Immunodeficiency Virus (HIV) trans-activator of transcription (Tat) protein wherein the modified amino acid sequence has greater than 85% sequence homology to an amino acid sequence selected from the group consisting of SEQ ID NO:2, SEQ ID NO:3 and SEQ ID NO:4. In another embodiment, the composition comprises the amino acid sequence of SEQ ID NO:3.

In one embodiment, a method of treating cancer is provided comprising administering a therapeutically effective amount of the Tat derivative polypeptide to a subject in need thereof; and causing cessation of growth of the cancer or regression of the cancer in the subject.

In another embodiment, a method of reducing tumor burden is provided comprising administering a therapeutically effective amount of the Tat derivative polypeptide of claim 1 to a subject in need thereof; and causing regression of the cancer in the subject.

In another embodiment, the Tat derivative polypeptide is administered in a plurality of doses.

In yet another embodiment, the administering step comprises a repetitive administration cycle wherein each cycle comprises administering a plurality of doses of the Tat derivative polypeptide in a defined time period followed by a rest period and wherein the cycle is repeated a plurality of times. In another embodiment, the administering step comprises a repetitive administration cycle wherein each cycle comprises administering a plurality of doses of the Tat derivative polypeptide in a defined time period followed by a administration of one or a plurality of doses of a therapeutic agent in a defined time period and wherein the cycle is repeated a plurality of times.

In another embodiment, the therapeutic agent is cyclophosphamide.

In yet another embodiment, the cancer is breast cancer. In another embodiment, the cancer is ovarian cancer.

In another embodiment, the Tat derivative polypeptide is at least 85% homologous to the amino acid sequence of SEQ ID NO:3.

BRIEF DESCRIPTION OF THE DRAWINGS

FIG. 6B depicts mice implanted SC with $2\times10^5$ SM1 breast cancer cells and treated SC with Nani-P2 (40 ng) on days 0, 7, 14 and 21. The difference in primary tumor growth between control and Nani-P2 treated SM1 animals was highly statistically significant (p<0.01***).

In FIG. 8A, two groups of 10 BALB/c mice were injected with $1\times10^4$ 4T1 cells in the mammary pad on day 0. One group was dosed with Nani-P2 (40 ng) weekly for three weeks beginning at day 14. A second group was PBS-treated and used as control. Tumor burden was highly significant by day 22 and remained so throughout the duration of the trial (p<0.01). Mice were sacrificed when tumor diameter reached 15 mm, at which time lung metastases were counted (FIG. 8B). Data represent total lung metastases as quantitated by two observers blinded to the treatment protocol (p<0.01).

DETAILED DESCRIPTION

Figure 1:
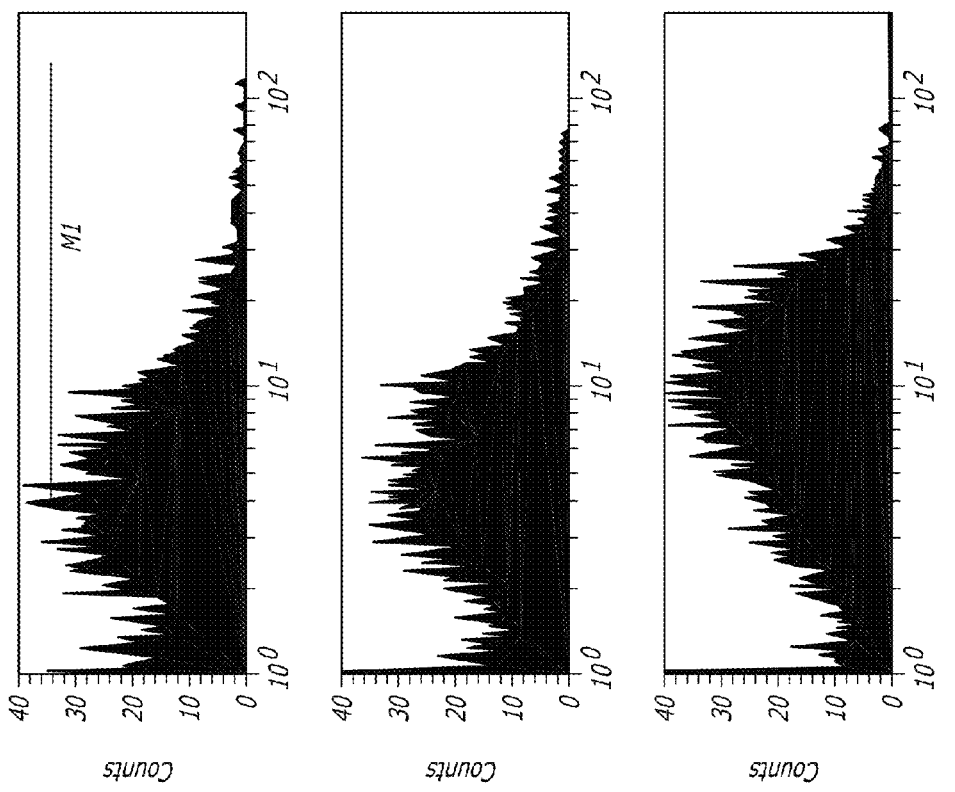
FIG. 1 depicts stimulation of human monocytes with Tat derivatives.
Figure 1:
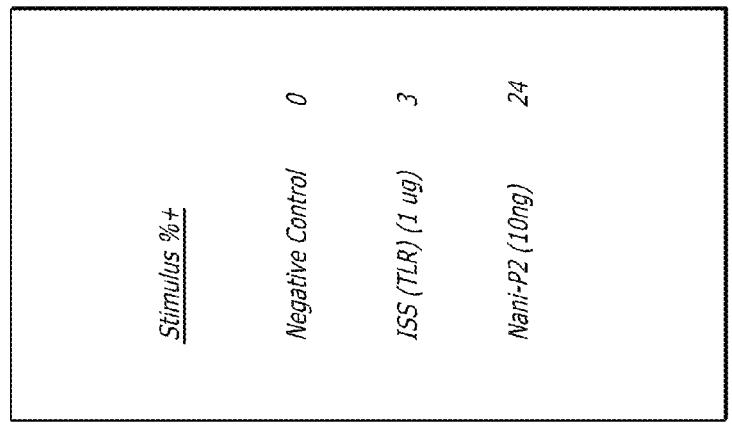

A series of artificial Human Immunodeficiency Virus (HIV) trans-activator of transcription (Tat) peptide derivatives has been designed which are highly active in animal models of breast cancer. The molecules are referred to herein as Tat derivatives or "Precision Immune Stimulants" (PINS) and comprise Tat molecules having deletion of elements that could be contributing to HIV-mediated immunosuppression. One of these derivatives, Nani-P2, causes regression of established metastatic breast cancer disease. At the doses reported here, no significant toxicity was associated with either the subcutaneous or intravenous administration of highly-purified (>95% pure) derivative.

Despite a relative abundance of tumor-specific antigens, breast cancer has proven to be a difficult target for immunotherapeutics. Evidence has accumulated that the refractory state of breast cancer, and other cancers, to immunotherapeutics could derive from immune suppression that accompanies established cancers. At least three separate epidemiological studies have shown that women with HIV infection and even Acquired Immunodeficiency Syndrome (AIDS) were paradoxically protected from developing breast cancer, even in late-stage disease when immunodeficiency is pronounced.

Based on molecular analysis, the Tat protein (SEQ ID NO:1) encodes four distinct linked peptide activities. This present disclosure describes polypeptide compositions that are derivatized from the canonical HIV-1 Tat structure in at least at the first or amino peptide, in a manner to enhance the immunotherapeutic potential of the polypeptide. The amino terminal portion of Tat includes a short peptide region from a nuclear transcription factor (TF) typically flanked by proline residues. This region determines, at least in part, how stimulatory or suppressive the Tat polypeptide is for cells of the immune system, particularly innate immune cells such as dendritic cells (DC) and macrophages (antigen-presenting cells or APCs). Consequently, it is predicted that modifications to the TF region can render the polypeptides more active in the therapy of cancer and other chronic diseases.

```
HIV-1 Tat protein
                                            (SEQ ID NO: 1)
MEPVDPRLEPWKHPGSQPKTACTTCYCKKCCFHCQVCFTKKALGISYGRK

KRRQRRRAPEDSQTHQVSPPKQPAPQFRGDPTGPKESKKKVERETETHPVD
```

In silico analysis discovered that HIV-1 Tat encodes a short SH3 binding domain identical to the sequence found in another TF protein, hairless (hr) that had previously been shown to have immunosuppressive properties in mice. Mice carrying the hr mutation develop an immune disregulation, now most commonly called "the TH1 to TH2 shift," that is the sine qua non of HIV-infected individuals who are progressing to AIDS. Further analysis established that SH3 binding sequence derived from the hr gene is a nearly invariant feature of Tat isolated from HIV-1, and a very consistent feature of HIV-2. Individuals infected by HIV-1 or HIV-2 progress to AIDS except in rare circumstances.

In contrast, primates infected by certain strains of simian immunodeficiency virus (SIV), a lentivirus closely related to HIV, rarely progress to AIDS or do so unpredictably. This observation coupled to the discovery of a putatively immunosuppressive hr TF fragment in immunosuppressive HIV-1 Tat suggested that some primates could have a different (or no) TF fragment at the amino terminus of SIV Tat. Tat from certain SIV-infected sooty mangabeys with an attenuated course of immunodeficiency has at its amino terminus a fragment from the TF TARA instead of the TF hr. TARA associates with the rho family of GTPase activators which have been implicated in certain oncogenic activations Animal trials with recombinantly-produced Tat protein derivatives in three different widely accepted murine models of breast cancer; 4T1, SM1 and TS/A provided support that these Tat derivatives are active in suppressing primary breast cancer growth in mice. Moreover, the most active derivative, Nani-P2, significantly inhibited the development of spontaneous 4T1 lung metastases and increased survival compared with control mice. Significantly, increased levels of IFN-γ production accompanied treatment of murine breast cancers with Tat derivatives. In studies when 4T1 breast cancers were seeded for fourteen days prior to the initiation of treatment, the Tat derivatives were equally as effective as when given at the time of tumor implantation when assessed by primary tumor growth, survival, and reduction in metastatic lung burden when compared to PBS-treated controls.

Synthetic Tat derivatives are immunostimulatory to APCs, have substantial activity against primary as well as established cancers in three widely-used murine mammary carcinoma models. In particular, one of the derivatives, Nani-P2, produced a dose- and route-dependant impact on primary tumor growth, lung metastasis formation, and survival in the aggressive, Her2(−) 4T1 breast cancer model. It is not surprising that decreased lung metastases correlate with improved survival, because lung metastasis is the leading cause of mortality in advanced breast cancer. Importantly, mice bearing established 4T1 breast tumors treated intravenously with Nani-P2 protein had highly significant tumor growth inhibition and survival benefits that extended out at least 36 days past the last dosing. In limited cases, total remissions were apparently observed that were more frequent with the less aggressive (SM1) and/or somewhat more immunogenic (TS/A) breast tumors. Delaying the administration of Nani-P2 post tumor implant had little negative effect on 4T1 tumor growth suppression, insofar as therapy (SC) initiated on day 0 after tumor cell injection shrank tumor burden on average 53%, while SC therapy begun on day 13, when tumor growth already averaged about 5 mm in diameter, decreased tumor burden on average 52% at its maximal effect. Taken together, these observations indicated that Nani-P2 can favorably impact advanced and Her2(−) human breast cancers in humans.

Furthermore, the Tat derivatives disclosed herein comprise fully human sequences. A gradual tachyphylaxis against the Tat derivatives is seen in mice administered more than three doses (data not shown), which may be substantially due to the host developing an inhibitory anti-derivative antibody response. As this kind of antibody response in humans could block DC activation thereby dramatically curtailing HIV replication, it apparently cannot easily build up in humans making it much less likely that a similar degree of tachyphylaxis at least as due to an antibody-based mechanism will be operative in human therapeutics.

The studies reported here used a protocol of three or four approximately weekly doses of Tat derivative given either IV or SC, with IV administration proving most efficacious for increasing survival and for reducing metastases. No toxicity was observed in over 250 mice given these compositions. The sensitivity of breast cancer to the Tat derivatives contrasts favorably when compared to the dose response curve of HERCEPTIN®, where 4-8 gm/kg is standard therapy. It is estimated that Tat derivatives will be up to 100-fold more bioactive in humans than mice, meaning that even lower doses associated with even less risk of toxicity could likely prove successful.

Figure 5A:
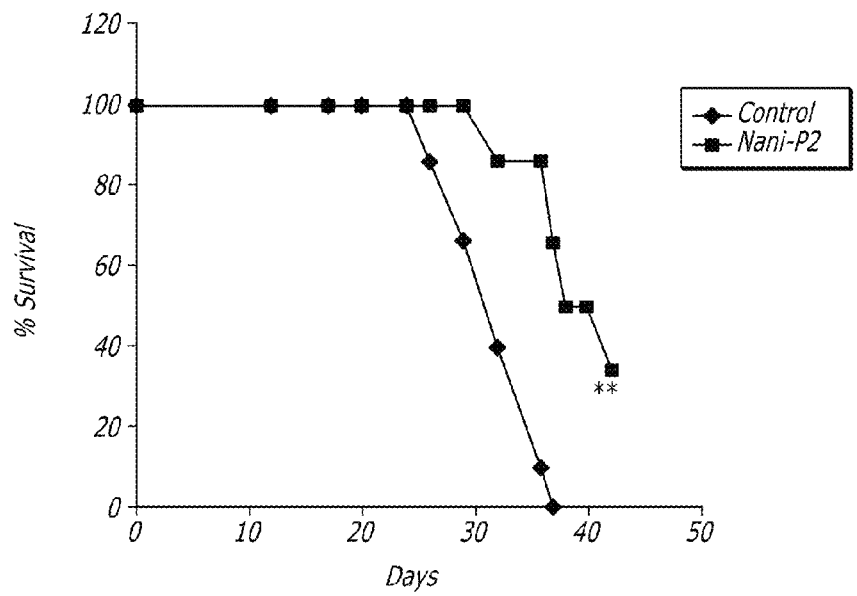
FIGS. 5A-B depict a Kaplan-Meier survival curve of Nani-P2 treatment of mice bearing 4T1 breast tumors. Mice were injected SC with $1\times10^4$ 4T1 cells in the mammary pad at day 0. Treatment was started at day 0 with four doses of Nani-P2 (40 ng) administered SC. At day 42, the treatment group had statistically significant better survival over controls () (FIG. 5A). In one group, therapy was delayed until day 13, at which time a series of three doses of Nani-P2 (40 ng) were administered weekly either intravenous (IV), SC into the draining lymph nodes or intratumoral (IT) (FIG. 5B). The survival benefit of IV Nani-P2 was highly statistically significant at day 47 (), while the survival benefit of SC Nani-P2 was also statistically significant (*).

Established herein is that the Tat derivatives activate the INF-γ arm of the anti-cancer T cell immune response (FIG. 5). Baseline levels of INF-γ secreted by splenocytes from mice treated with Nani-P2 are 8-fold higher than that from control mice treated with PBS. IFN-γ secretion in response to Tat derivative treatment in vivo could be additionally augmented (up to 53×) in vitro by innate immune agonists GM-CSF and IL-4, while splenocytes from control mice remain suppressed even after attempts to co-stimulate with high-dose GM-CSF and/or IL4.

While the disclosed Tat derivatives are countersuppressive agents with "stand alone" efficacy in both advanced and early murine breast carcinoma, these observations moreover support the prospect that the Tat derivatives can synergize with other countersuppressive anti-cancer therapeutics currently in clinical development that may have a restricted effect in the face of advanced tumor burden and accompanying severe immunosuppression.

A more immunogenic breast cancer model (SM1) and/or a breast tumor with an immunodominant epitope (TS/A) have a relatively high regression rate after Tat derivative therapy, while the "non-immunogenic" 4T1 model is more refractory. This is consistent with a model that immune suppression is a dominant factor in breast cancer progression, and in fact may be contributory to breast cancer invasiveness. This model is supported by the observation that 4T1 expresses several common breast cancer antigens, including lactadherin and androgen binding protein, at high levels against which the immune response is apparently fully suppressed absent Tat derivative-induced countersuppression. Taken together, these observations raise the possibility that the Tat derivatives, when administered to healthy at-risk women along with one or several common human breast cancer antigens, could ultimately be developed into a prophylactic anti-breast cancer vaccine.

In additional embodiments, disclosed herein is the use of conservatively modified variants of the Tat derivatives. The variants described herein maintain the biological activity of the parent or source molecule.

As used herein the term "conservatively modified variants" refers to variant peptides which have the same or similar biological activity of the original peptides. For example, conservative amino acid changes may be made, which although they alter the primary sequence of the protein or peptide, do not alter its function. Conservative amino acid substitutions typically include substitutions within the following groups: glycine and alanine; valine, isoleucine, and leucine; aspartic acid and glutamic acid; asparagine and glutamine; serine and threonine; lysine and arginine; phenylalanine and tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g. by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides disclosed herein are not limited to products of any of the specific exemplary processes listed herein.

In addition to substantially full length polypeptides, the present disclosure also provides for biologically active fragments of the polypeptides.

As used herein, amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present disclosure. As readily recognized by those of skill in the art, various ways have been devised to align sequences for comparison, e.g., Blosum 62 scoring matrix, as described by Henikoff and Henikoff in Proc. Natl. Acad Sci. USA 89:10915 (1992). Algorithms conveniently employed for this purpose are widely available (see, for example, Needleman and Wunsch in J. Mol. Bio. 48:443 (1970).

Therefore, disclosed herein are amino acid sequences 85%, 90%, 95%, 98%, 99% or 100% identical to the Tat derivatives disclosed in SEQ ID NOs. 1-4.

The following expression systems are suitable for use in expressing the disclosed Tat derivatives: mammalian cell expression systems such as, but not limited to, insect cell expression systems such as, but not limited to, Bac-to-Bac expression system, baculovirus expression system, and DES expression systems; and *E. coli* expression systems including, but not limited to, pET, pSUMO and GST expression systems. In another embodiment, the Tat derivatives are expressed with a 6-His tag useful for isolation of the polypeptide. 6-His tag purification systems are known to persons of ordinary skill in the art.

"Therapeutically effective amount" is intended to qualify the amount required to achieve a therapeutic effect.

The disclosed Tat derivatives are immune-stimulating polypeptides which are useful in many types of cancers. In one embodiment, the Tat derivatives are useful in treating a type of cancer including, but not limited to, breast cancer, melanoma, ovarian cancer, lung cancer, pancreatic cancer, myeloma, colorectal cancer, renal cancer, lymphoma and colon cancer.

In another embodiment, the cancer is breast cancer. In yet another embodiment, the cancer is ovarian cancer.

The present disclosure is also directed to pharmaceutical compositions comprising the above-described Tat derivative polypeptides. Dosages and desired drug concentrations of the disclosed pharmaceutical compositions may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. In one embodiment, the disease is present. In another embodiment, the life of a cell or an individual is prolonged due to the methods described herein.

The above-described Tat derivative polypeptides can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, nasal, lingual, sublingual, buccal, intrabuccal, intravenous, subcutaneous, intramuscular and pulmonary administration can be made without undue experimentation by means well known in the art, for example with an inert diluent or with an pharmaceutically acceptable carrier. For the purpose of therapeutic administration, the pharmaceutical compositions may be incorporated with excipients and used in the form of tablets, troches, capsules, elixirs, suspensions, solutions, syrups, and the like. A "pharmaceutically acceptable carrier" means any of the standard pharmaceutical carriers. Examples of suitable carriers are well known in the art and may include but are not limited to any of the standard pharmaceutical carriers like phosphate buffered saline solutions, phosphate buffered saline containing Polysorb 80, water, emulsions such as oil/water emulsion, and various types of wetting agents. Other carriers may also include sterile solutions, tablets, coated tablets, and capsules. Typically such carriers contain excipients like starch, milk, sugar, certain types of clay, gelatin, stearic acid or salts thereof, magnesium or calcium stearate, talc, vegetable fats or oils, gums, glycols, or other known excipients. Compositions comprising such carriers are formulated by well known conventional methods.

The Tat derivative polypeptide compositions can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Transdermal administration includes percutaneous absorption of the composition through the skin. Transdermal formulations include patches, iontophoresis devices, ointments, creams, gels, salves and the like.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The Tat derivative polypeptide compositions of the present disclosure may be administered in a therapeutically effective amount, according to an appropriate dosing regimen. As understood by a skilled artisan, the exact amount required may vary from subject to subject, depending on the subject's species, age and general condition, the severity of the infection, the particular agent(s) and the mode of administration. In some embodiments, about 0.001 mg/kg to about 50 mg/kg, of the composition based on the subject's body weight is administered, one or more times a day, to obtain the desired therapeutic effect. In other embodiments, about 1 mg/kg to about 25 mg/kg, of the composition based on the subject's body weight is administered, one or more times a day, to obtain the desired therapeutic effect.

The total daily dosage of the compositions will be determined by the attending physician within the scope of sound medical judgment. The specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compositions may also be employed in combination therapies. That is, the compositions presently disclosed can be administered concurrently with, prior to, or subsequent to, one or more other desired compositions, therapeutics, treatments or medical procedures. The particular combination of therapies administered will be determined by the attending physician and will take into account compatibility of the treatments and the desired therapeutic effect to be achieved. It will be appreciated that therapeutically active agents utilized in combination may be administered together in a single composition, treatment or procedure, or alternatively may be administered separately.

In another embodiment, repetitive, or frequent, dosing of the disclosed Tat derivatives is contemplated that could run ahead of tachyphylaxis, as well as reverse the immunosuppressive tide established during breast cancer progression. Frequent dosing is one procedure used for example in allergy therapy that can support immunological tolerance to an agent. Once the Tat derivative can be used to regain immunoreactivity to a breast tumor, then other immunotherapeutics that have lost benefit due to advanced disease could potentially regain efficacy. In a second protocol, chemotherapeutic regimens are used that could release a shower of tumor antigens in alternation with Tat derivative immunotherapy. As advanced stage human breast cancers are multiply drug resistant, radiotherapy could be a practical alternative in human trials.

The number of repeated doses of the Tat derivatives can be established by the medical professional based on the response of the patient to the doses. In one embodiment, the Tat derivative is administered once every three days for 3 doses in a ten day period. This administration scheme is then repeated for a plurality of cycles. The present disclosure envisions a variety of different administration schemes wherein the Tat derivative is administered multiple times within a selected time frame and then the administration scheme is repeated for a plurality of cycles. In another embodiment, administration of the Tat derivative can be alternated with administration of one or more other anti-cancer, immunomodulatory or immunosuppressive agents. In one embodiment, the immunosuppressive agent is cyclophosphamide.

EXAMPLE 1

Design and Production of Tat Derivatives

Three exemplary Tat derivatives are disclosed herein, each of which replaces the TF hr fragment in a different manner. The underlined portions of the sequences represent the sequences between the prolines.

```
Nani-P1-
                                (MPM1; SEQ ID NO: 2)
MEPVDANLEAWKHAGSQPRKTACTTCYCKKCCFHCQVCFTRKGLGISYG

RKKRRQRRRAPQDSQTHQASLSKQPASQSRGDPTGPTESKKKVERETET

DPFD

Nani-P2-
                                (ASH4; SEQ ID NO: 3)
MDPKGEEDQDVSHQDLIKQYRKPRTACNNCYCKKCCFHCYACFLRKGLG

ITYHAFRTRRKKIASADRIPVPQQSISIRGRDSQTTQESQKKVEEQAKA

NLRISRKNLGDETRGPVGAGN.

Nani-P3-
                                (TMPD5; SEQ ID NO: 4)
METPLKEQENSLESCREHSSSISEVDVPTPVSCLRKGGRCWNRCIGNTR

QIGSCGVPFLKCCKRKPFTRKGLGISYGRKKRRQRRRAPQDSQTHQASL

SKQPASQSRGDPTGPTESKKKVERETETDPFD
```

SH3 binding proteins contain a series of internal prolines required for TF function. Nani-P1 has removed the internal prolines, which are each substituted as alanine, rendering the SH3-binding site inactive. This alteration cripples the entire Tat protein as a TF, because it is now produced predominantly as an intracytoplasmic protein, unlike the other Tat derivatives.

Nani-P2 has a derivatized Tat amino terminus from an African Green Monkey variant SIV with low pathogenicity in the host. Only the carboxyl flanking proline is conserved in this sequence.

In Nani-P3, a serine-rich TARA homology sequence replaces the SH3 binding sequence as an amino TF peptide flanked by prolines. The Tat was originally sequenced from a low pathogenic variant SIV in macaques and sooty mangabey monkeys.

EXAMPLE 2

In Vitro Activity of Tat Derivatives

Figure 2:
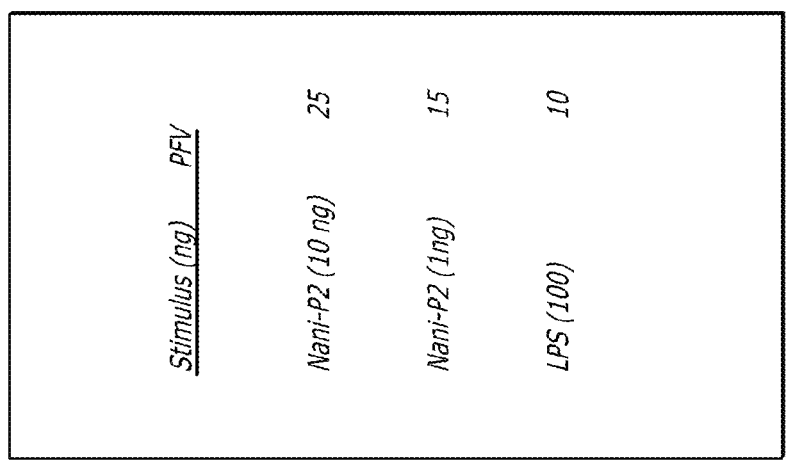
FIG. 2 depicts a dose-response curve of stimulation of human monocytes with Tat derivatives.
Figure 2:
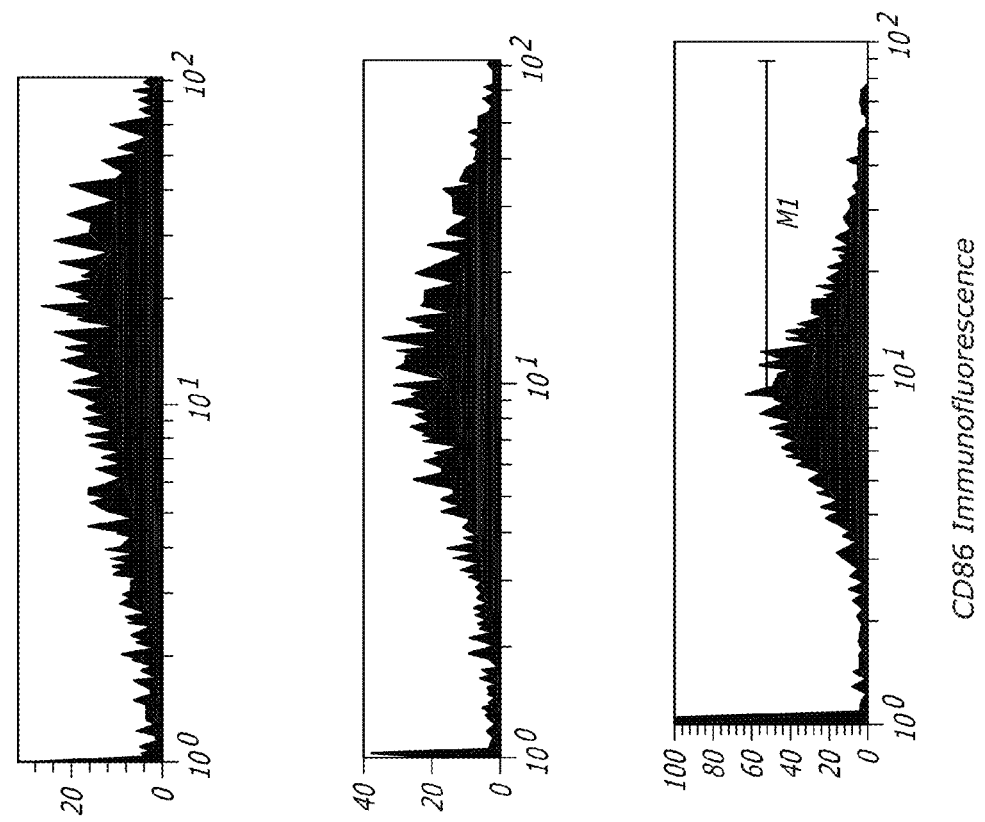

Human monocytes were cultured for 24-28 hours with a Tat derivative (Nani-P2), an immunostimulatory sequence (ISS) of a toll-like receptor (TLR) (FIG. 1) or lipopolysaccharide (LPS) (FIG. 2) and the cells were then washed and stained with fluorescent-labeled CD86. The Tat derivative stimulated higher expression of CD86 than either ISS (TLR) or LPS.

EXAMPLE 3

Evaluation of Tat Derivatives in Mouse Models of Breast Cancer

Materials and Methods
Animals.
Female BALB/c mice 6 to 8 weeks old were purchased from the Jackson Laboratory (Bar Harbor, Nebr.). Mice were acclimated for at least 1 week before use. Mice were kept in pathogen-free conditions at the Animal Maintenance Facility of the Columbia University of Medical Center and all experiments were approved by the Institutional Animal Care and Use Committee of Columbia University of Medical Center.

Cell Lines.
4T1 cells, a 6-thioguanine-resistant cell line derived from a BALB/c spontaneous mammary carcinoma was obtained from ATCC; TS/A, a murine adenocarcinoma cell line was provided by Dr. Sandra Demaria (Demaria S. et al. Clin Cancer Res. 11:728-34, 2005); and SM1, the BALB/C-derived mammary carcinoma was kindly was provided by Dr. James Allison, University of California, Berkeley. All tumor cell lines were cultured in DMEM, supplemented with 2 mM L-glutamine, 10 mM HEPES, 150 units/ml penicillin/streptomycin, 10% heat-inactivated FCS (Invitrogen), 50 $\mu$M 2-mercaptoethanol (Sigma), and 50 mg/L gentamicin (Lanza).

Tumor Challenge and Treatment.
BALB/c were injected (SC) with $1 \times 10^4$ 4T1, $1 \times 10^5$ TS/A or $2 \times 10^5$ SM1 cells, respectively, in the left mammary pad on day 0. Immunotherapy was performed by directly injecting a Tat derivative into the right flank at 0, 7, 12, and 17 days after establishment of tumors. The control group received PBS injection. In some experiments, when all of mice had an established measurable tumor (3-5 mm diameter at 14 days after tumor injection), the animals were randomly assigned to various treatment groups as indicated. Tumor burden (tumor volume) was measured and recorded three times weekly. Animals were sacrificed when tumors reached a volume of 15 mm in diameter and the tumors harvested and weighed.

Detection of Lung Metastases.
Lungs were examined for 4T1 metastases as previously described (Pulaski B. et al. Cancer Res. 60:2710-2715, 2000). Primary 4T1 tumors that have been established for 2-3 weeks in BALB/c mice metastasize to the lungs in a very large majority of animals. Briefly, mice were sacrificed according to IACUC guidelines established at the start of the trials, the lungs removed, and tumor nodules on the surface of the lungs were enumerated with the naked eye by two independent investigators blinded to the treatment protocols.

ELISA Analysis of IFN-$\gamma$ Production by Immune Spleen Cells.
Splenocyte secretion of IFN-$\gamma$ was assessed by an OPTEIA® ELISA kit (BD Biosciences). Briefly, spleen cells ($1 \times 10^5$/well) from 4T1 tumor-bearing mice were cultured with or without $5 \times 10^3$/well mitomycin C (50 $\mu$g/ml)-treated 4T1 cells (used to provide tumor antigens) in DMEM in at a 20:1 E:T (effector:tumor) ratio with IL-2 (50 ng/mL) and GM-CSF (100 ng/ml) in 96-well plates. Supernatants were collected after 72 hr and kept frozen at $-80°$ C. until analysis without loss of activity. IFN-$\gamma$ was measured in cell-free supernatants of duplicate wells by ELISA according to the manufacturer's instructions. Tumor-specific IFN-$\gamma$ production was calculated by subtracting the background values measured in supernatants of spleen cells cultured with medium alone and optical density (OD) values were converted to pg/ml amounts of IFN-$\gamma$ using a recombinant IFN-$\gamma$ standard curve. Stimulation index (SI) was calculated as the ratio of IFN-$\gamma$ in stimulated versus control cultures.

Statistical Analysis.
Data were statistically analyzed using Student's t-test (Graph Pad Prism version 5; GraphPad). Data from animal survival experiments were statistically analyzed using log-rank test (Graph Pad Prism version 5).

Results
The therapeutic effect of systemic administration of synthetic, Tat-derived compositions in murine models of breast cancer was investigated. To compare the relative protection conferred by a small panel of different derivatives against primary breast tumor growth, female BALB/c mice were injected with $1 \times 10^4$ 4T1 breast tumor cells SC into the mammary pad, and then treated with 400 ng partially-purified Tat derivatives at day 0, 7, 14 and 21 (SC injection in PBS) into the draining axillary lymph nodes.

Figure 3A:
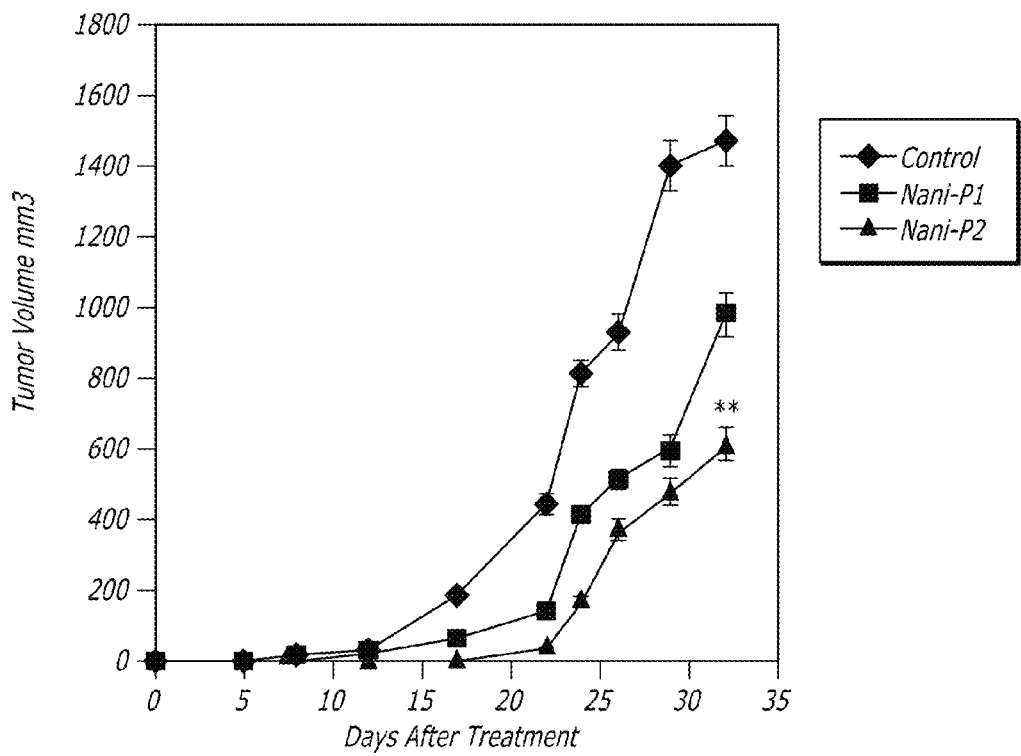
FIGS. 3A-B depict the effect of therapy with Tat derivatives on 4T1 tumor growth in vitro. BALB/c mice injected with $1\times10^4$ 4T1 tumor cells were treated with Nani-P1 or Nani-P2 (400 ng, subcutaneous [SC]) (FIG. 3A) or Nani-P3 (400 ng or 2 µg, SC) (FIG. 3B) on days 0, 7, 14 and 21 after injection of tumor cells. The control group was treated with PBS. Data represents mean tumor volume; bars±SE. Each group contained 10 mice. From day 15, the differences between the control group and groups treated with Nani-P1 or Nani-P2 were significant (p<0.05). The differences between control and Nani-P2 or Nani-P2 was highly significant starting at day 22 (p<0.01). There was no difference between Nani-P3 (either dose) and controls.
Figure 3B:
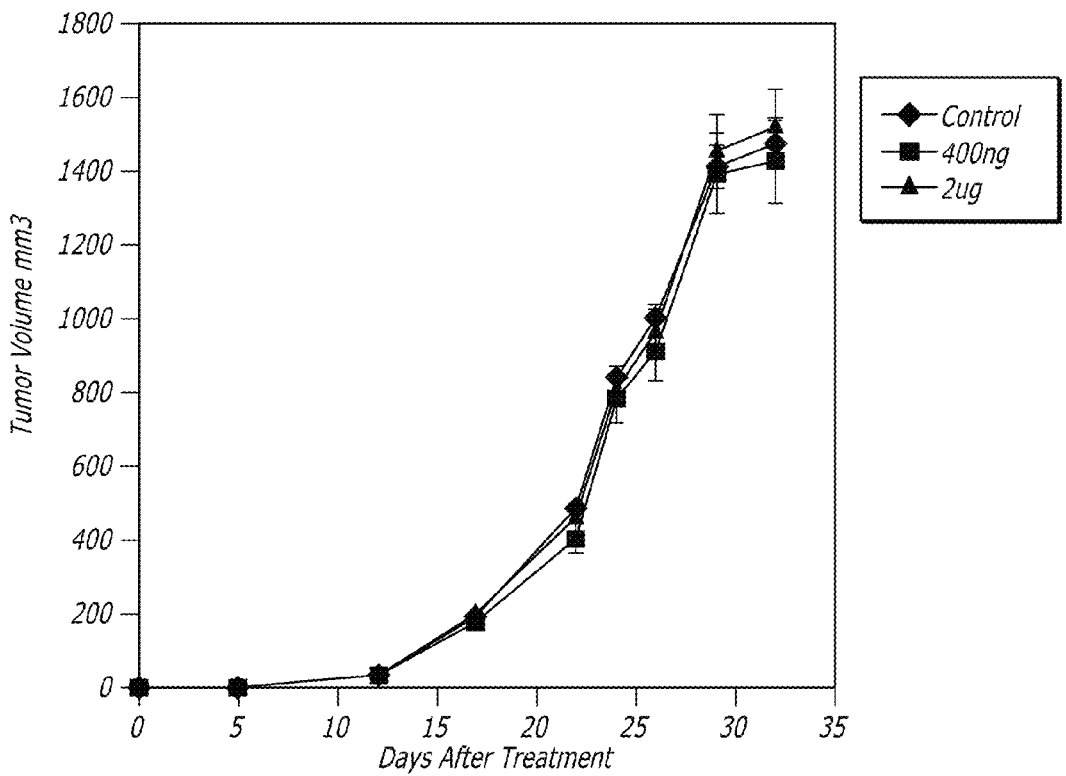

Two of the derivatives, Nani-P1 and Nani-P2, significantly reduced tumor burden when compared to control mice receiving PBS injections alone, with this difference first becoming apparent at 15 days after tumor implantation (FIG. 3A, day 15 $p<0.05$). By contrast a third derivative, Nani-P3, produced and partially purified with the same protocol as the others, was less effective at suppressing 4T1 primary tumor growth even at five-fold higher doses (2 $\mu$g, FIG. 3B) or for extending survival (not shown). These results effectively ruled out that contaminants in preparation contributed to anti-tumor efficacy, particularly insofar as subsequent trials were performed with highly purified (>95% pure) materials at much lower doses. The efficacy of Nani-P2 was significantly more sustained than Nani-P1, so that at day 21 (the final dosing), the difference in primary tumor burden between Nani-P2 and Nani-P1-treated tumors became 18 mm$^3$ and was highly statistically significant ($p<0.01$). This effect persisted throughout the remainder of this trial despite no further therapy.

Figure 4:
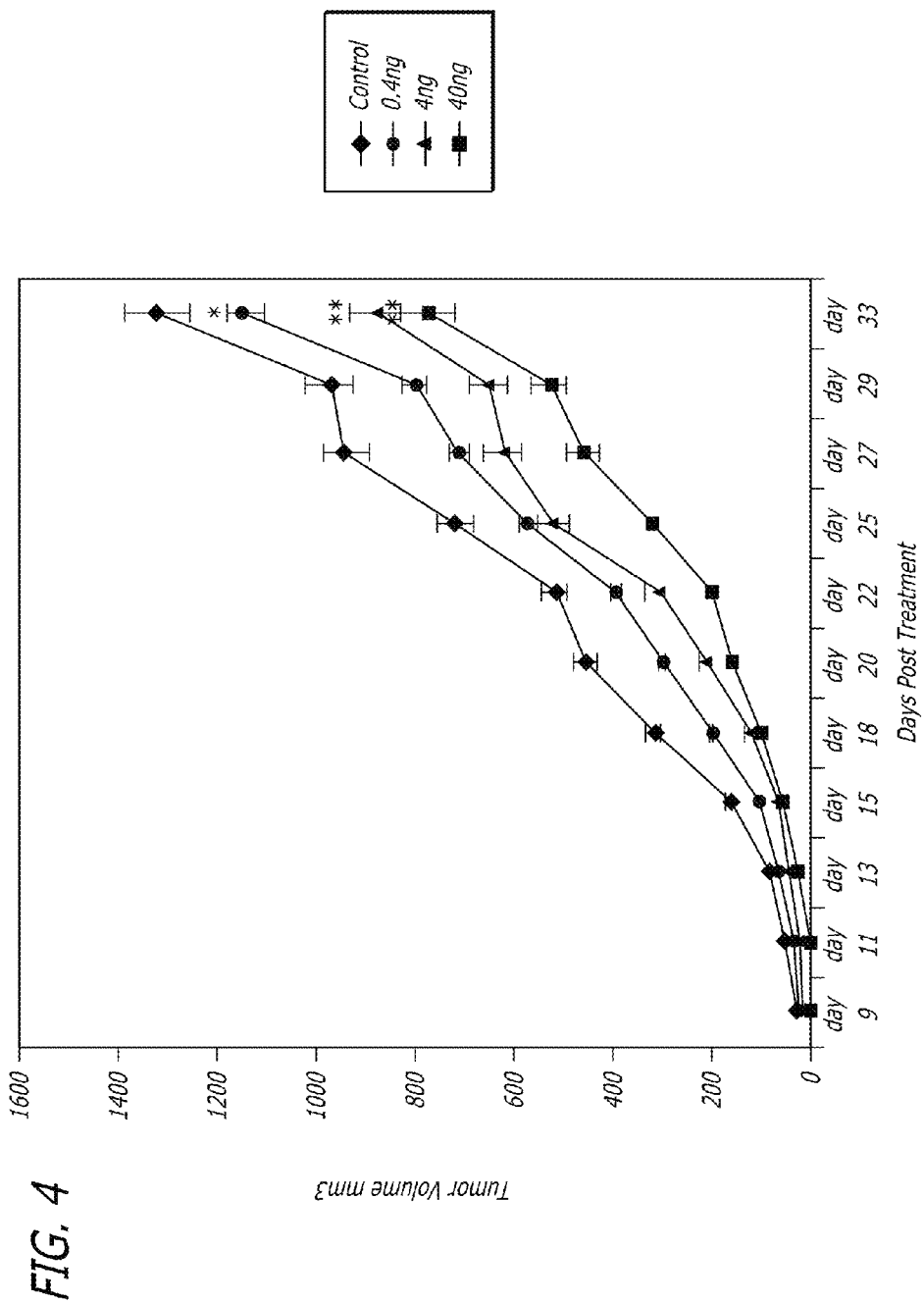
FIG. 4 depicts a dose response curve for the effects of purified Nani-P2 on 4T1 breast tumor growth in vivo. Four groups of ten BALB/c mice each were implanted with $1\times10^4$ 4T1 cells. Three groups were given escalating doses of 0.4 ng, 4 ng and 40 ng per mouse, respectively, in the left flank four times over 21 days. The fourth, control group was injected in the left flank with PBS. Data represent mean tumor volume. The differences between the control group and 0.4 ng dose was significant (p<0.5*) and the difference between control and 4 ng or 40 ng Nani-P2 treated groups was highly significant (p<0.1, p<0.01).

The breast tumor growth inhibitory effect of highly-purified Nani-P2 on 4T1 tumors was dose-dependent, with significant effects apparent following the SC administration of as little as 0.4 ng of compound (FIG. 4). Increasing the dose of Nani-P2, administered SC in the draining axillary flank, by logarithmic increments from 0.4 ng to 40 ng per dose progressively inhibited 4T1 breast tumor growth. The more robust 4T1 growth inhibition at higher doses of Nani-P2 between 0.4 ng to 40 ng was statistically significant ($p<0.01$), while increasing the dose to 400 ng and even 2 $\mu$g resulted in no further anti-tumor efficacy (data not shown). Importantly, no toxicity was observed following the SC or IV administration of 40 ng of Nani-P2 in multiple trials using multiple dosing schedules. A dose of 40 ng Nani-P2 was selected for further study.

To determine whether Nani-P2 treatment could extend survival in addition to shrinking primary tumors in mice, treatment protocols using various dosing schedules and routes (SC, IV or IT) of administration of 40 ng Nani-P2 were performed. Cohorts of ten mice per group were followed for length of survival, as assessed by use of the Kaplan-Meier product limit method. As per Columbia University Medical Center Animal Facility regulations, each mouse was euthanized at a mean tumor diameter of approximately 15 mm, or earlier if the mouse became moribund, making one of these two outcomes the defining criteria for fatality.

In the first trial evaluating Nani-P2, SC treatment was initiated simultaneously to tumor implant. The median survival time for control (PBS treated) mice was 30 days and 100% fatality occurred by day 36. With Nani-P2 administration (4 doses over 21 days), 35% of treated mice were still alive at day 48 (p<0.001, FIG. 5A) at which point all of the mice were sacrificed due to primary tumor burden.

Figure 5B:
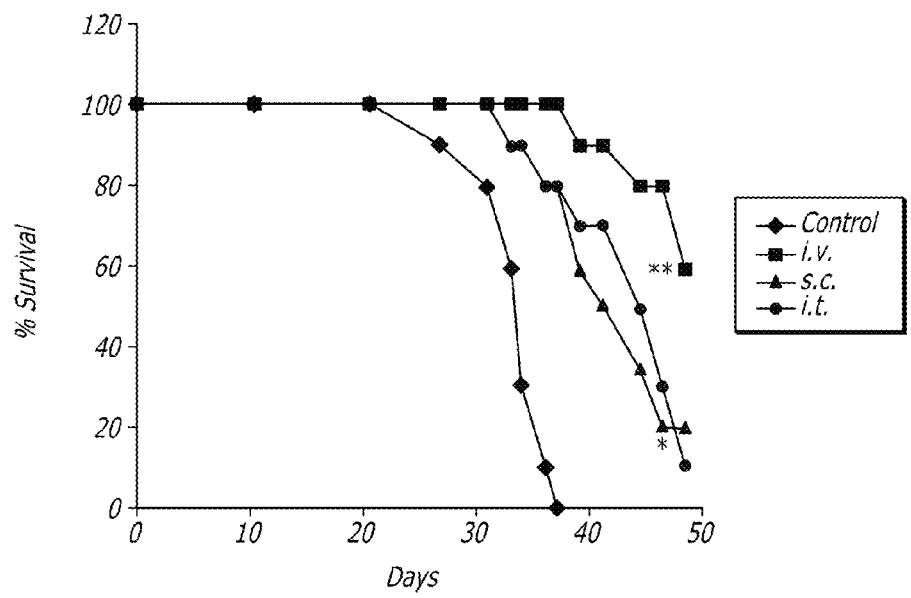

In a second survival trial, the tumors were allowed to become established for fourteen days to better assess efficacy in metastatic disease, after which three cycles of Nani-P2 therapy were administered weekly by one of several routes (SC, IV or IT) to compare relative efficacy for each route of dosing (FIG. 5B). Similar to the previous trial, median survival of control (PBS-treated SC) mice was 32 days, with 100% fatality by day 36. Survival was extended by the IV administration of Nani-P2 (p<0.005, FIG. 5B) with 60% survival at day 47, compared with 20% survival of SC treated mice at day 47 (p<0.05). Intratumoral administration of compound was slightly inferior to SC administration.

Figure 6A:
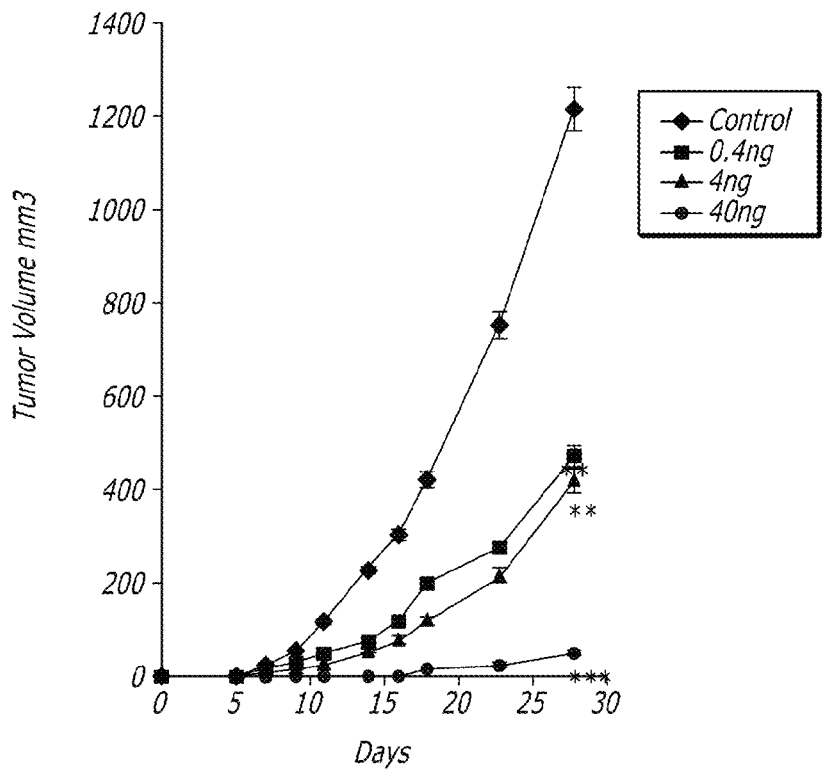
FIGS. 6A-B depict the anti-tumor activity of Nani-P2 in TS/A and SM1 breast carcinoma models. Mice were implanted SC with $1\times10^5$ TS/A breast cancer cells (FIG. 6A) and treated with escalating doses of SC Nani-P2 (0.4, 4 and 40 ng). Even at the lowest dose, the primary anti-cancer difference was highly significant (p<0.01), while the 40 ng dose was also highly significant (p<0.01*).
Figure 6B:
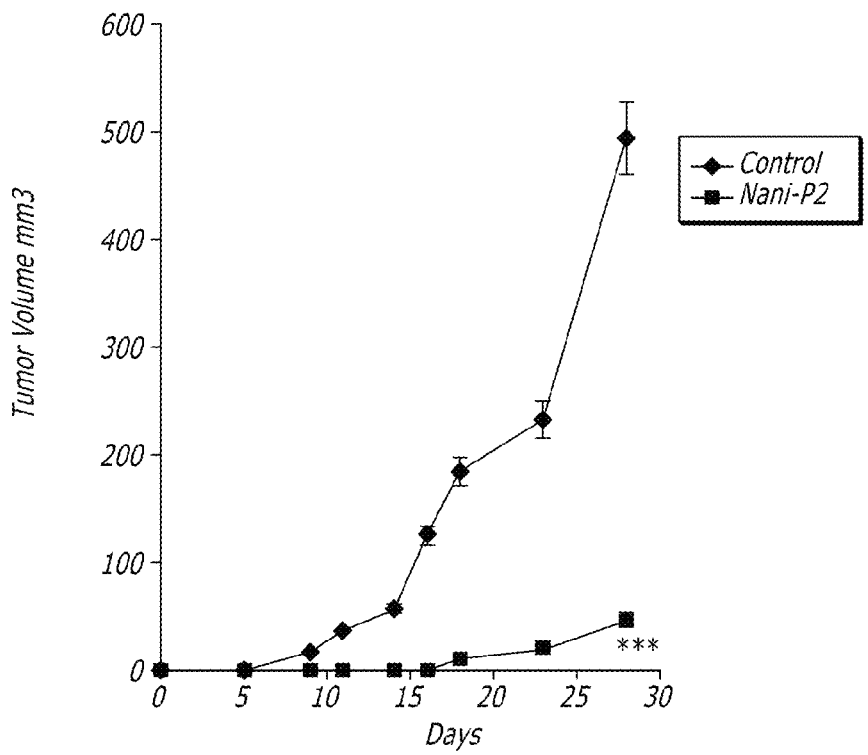

The 4T1 murine mammary tumor model was chosen for study because it is an aggressive and rapidly invasive tumor; it is routinely metastatic at fourteen days post-implant by which time it is difficult to treat. To learn whether the efficacy of Nani-P2 could extend to other murine breast tumor models, two additional mammary tumors, TS/A and SM1 were studied (FIG. 6). TS/A primary mammary tumors were approximately as aggressive as 4T1, reaching a tumor volume of 15 mm at 30 days (FIG. 6A). However, the TS/A tumors were considerably more responsive to Nani-P2 treatment, with an approximate 50% suppression of growth after treatment with 0.4 ng Nani-P2, and a 40% total remission rate at 30 days.

The SM1 mammary carcinoma model (FIG. 6B) is initially less aggressive as a primary tumor, and deaths appear to be through mechanisms other than metastatic disease. By day 30 of treatment, SM1 tumors reached a mean volume approximately 33% smaller than either TS/A or 4T1. This indicated a heightened sensitivity of the SM1 tumor to Nani-P2 immunotherapy as compared to 4T1, such that tumor growth was suppressed in 100% of animals for 16 days, and 40% of animals remained in remission even at 28 days following implant and fully one week after termination of the regimen.

Figure 7:
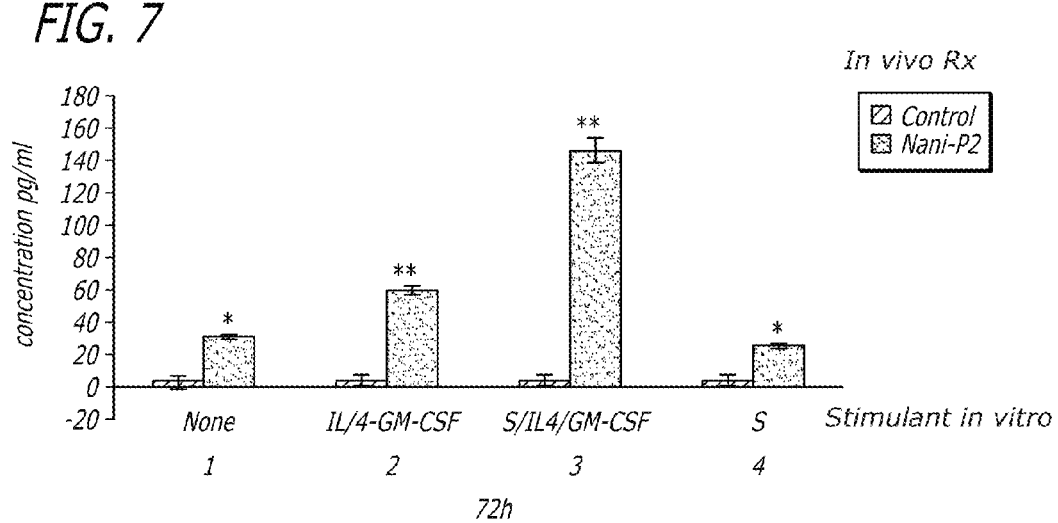
FIG. 7 depicts INF-γ production from spleen cells of mice bearing 4T1 breast tumors. BALB/c mice were injected SC with $1\times10^4$ 4T1 cells. Control animals received weekly injections of PBS, while the Nani-P2 treatment comprised once weekly SC injections (40 ng) initiated at day 0 and continued for 4 weeks. On day 33, when control mice were at endstage, the mice were sacrificed, the spleens harvested and frozen as single cell suspensions until time of assay. Spleen cells ($2\times10^5$) and $1\times10^4$ mitomycin C-treated (50 µg/ml for 30 min) 4T1 stimulator cells (S) were plated into 96-well plates. After 72 hr of stimulation, the supernatants were collected and IFN-γ concentration was determined using a commercial IFN-γ ELISA kit. IFN-γ production was significantly (p<0.05*) higher in cultures of spleen cells from Nani-P2-treated mice under all conditions of in vitro culture. 1: no restimulation; 2: IL-4 (50 ng/ml)/GM-CSF (100 mg/ml); 3: stimulator cells/IL-4/GM-CSF; 4: stimulator cells only. Addition of in vitro agonists IL-4 and GM-CSF (2 and 3) induced highly significant increases in IFN-γ production (p<0.01**).

To determine whether cytotoxic T-lymphocytes play a role in tumor rejection induced by Nani-P2 therapy, an IFN-γ ELISA assay (FIG. 7) was performed to compare spleen cells of 4T1 tumor-bearing mice treated either without (Control) or with Nani-P2 (FIG. 7). Spleens were removed under sterile conditions and prepared as described elsewhere (duPre'S. et al. Exp. Mol. Path. 85:174-188, 2008). Briefly, spleens were homogenized and splenocytes, as a rich source of systemic cytolytic T cells and APCs, were co-cultured with mitomycin C-treated 4T1 stimulator cells to induce recall immune responses. Control wells were cultured with medium alone.

IFN-γ concentrations, a standard surrogate for CTL activation, were quantitated by commercial ELISA (BD Biosciences). INF-γ production was significantly (p<0.01**) higher in cultures of spleen cells taken from Nani-P2-treated BALB/c mice under all conditions of assay. IFN-γ activity in Nani-P2-treated but not in control animals could be enhanced by the addition of IL-4 and GM-CSF (p<0.05) under conditions shown to promote DC differentiation, and could be even further augmented if tumor stimulators were added back at the initiation of culture (stimulation index=53 vs control, 3S+IL4+GM-CSF) demonstrating the potency of Nani-P2 in synergy with other CTL agonists.

Figure 8A:
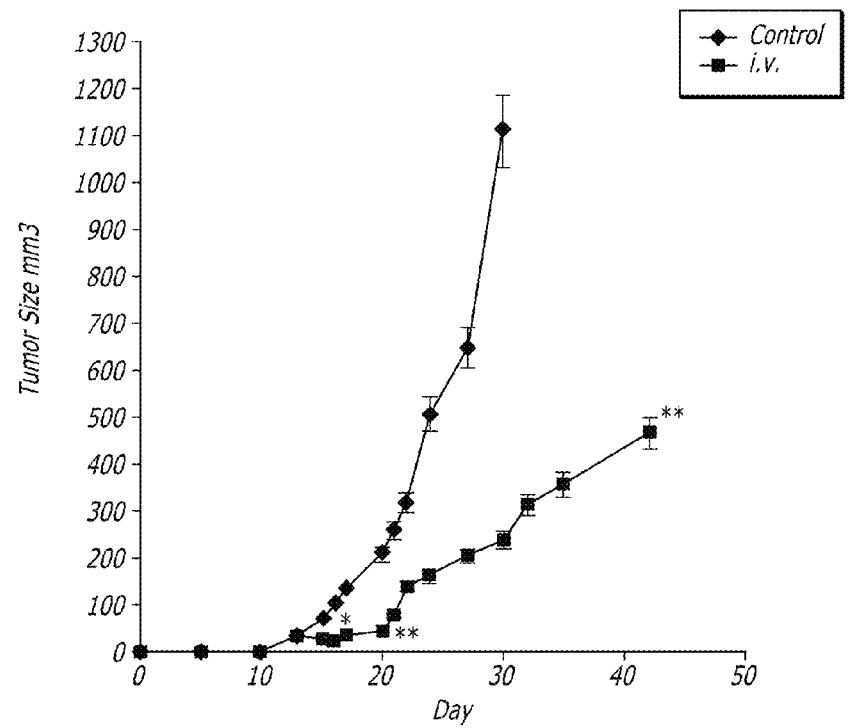
FIGS. 8A-B depict regression of established 4T1 breast tumors and inhibition of lung metastasis by Nani-P2 treatment.
Figure 8B:
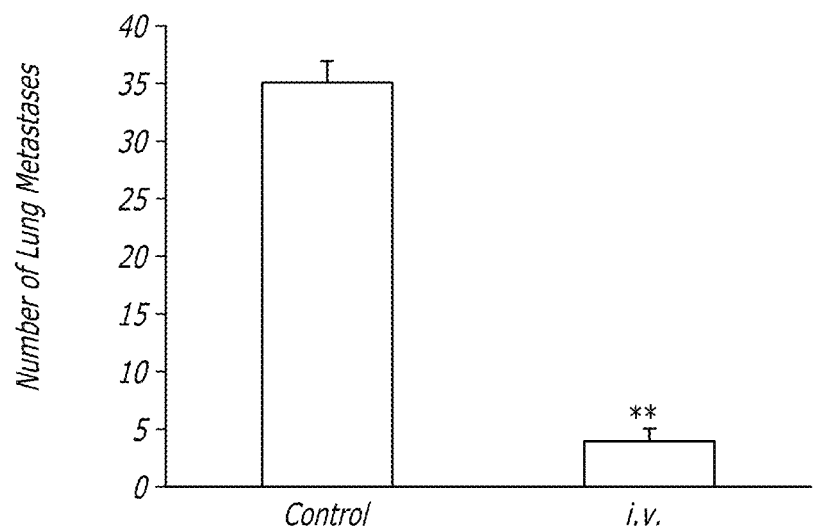
Figure 9:
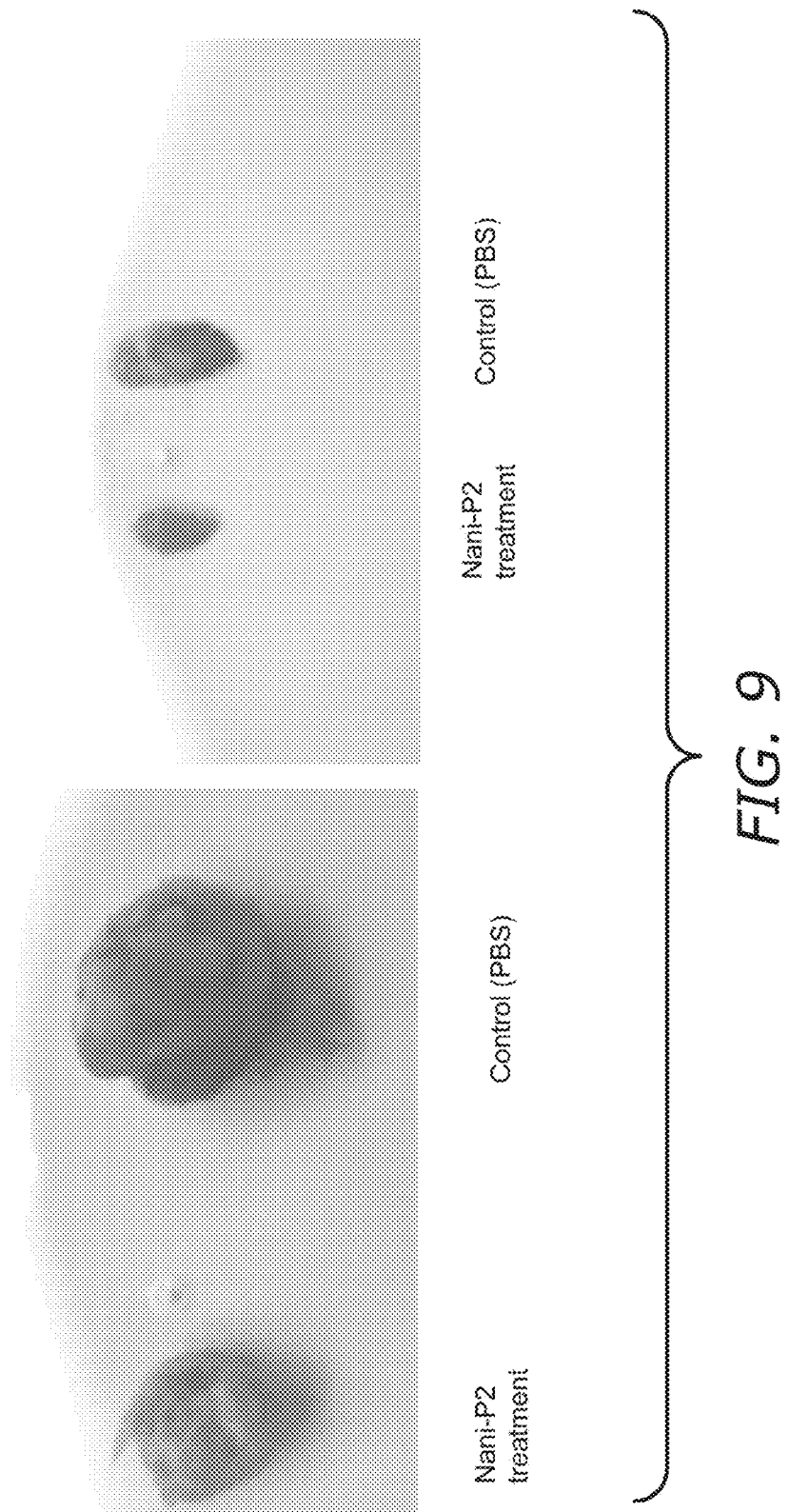
FIG. 9 depicts 4T1 tumor growth and lung metastasis in BALB/c mice. Two groups of 10 BALB/c mice were implanted subcutaneously (SC) with either $1\times10^4$ 4T1 cells, mice injected IV with 40 ng Nani-P2 or PBS. On day 28 of treatment, the mice were killed and the lungs and tumor were removed and tumor nodules were counted by eye. Photographs of the tumors and lungs, which were representative of 10 mice, are shown. Whitish tumor lesions can be observed on the surface of the lungs. Three experiments yielded similar results.

To further investigate the efficacy of Nani-P2 against established and metastatic breast cancer, 4T1 cells were injected SC in the abdominal mammary gland of mice and treatment was delayed until such time that the tumors had metastasized to the lungs and averaged 3.5 mm in size (FIG. 8A, day 13), corresponding to a 2.4 cm or stage T2 human breast tumor. Mice were followed for tumor growth (FIG. 8A) and lung metastases (FIG. 8B). At necropsy, animals that had received Nani-P2 treatment showed a dramatic reduction in the visible number of lung metastases when compared against controls (FIG. 9). The average number of grossly visible tumor nodules in the lungs of mice treated IV with Nani-P2 was seven, compared to the PBS-control group, which had an average of 35.3 (p<0.01**). This corresponded to a less aggressive appearance of primary tumor, as well as lung metastases that were on average much smaller in size (FIG. 8B).

Figure 10:
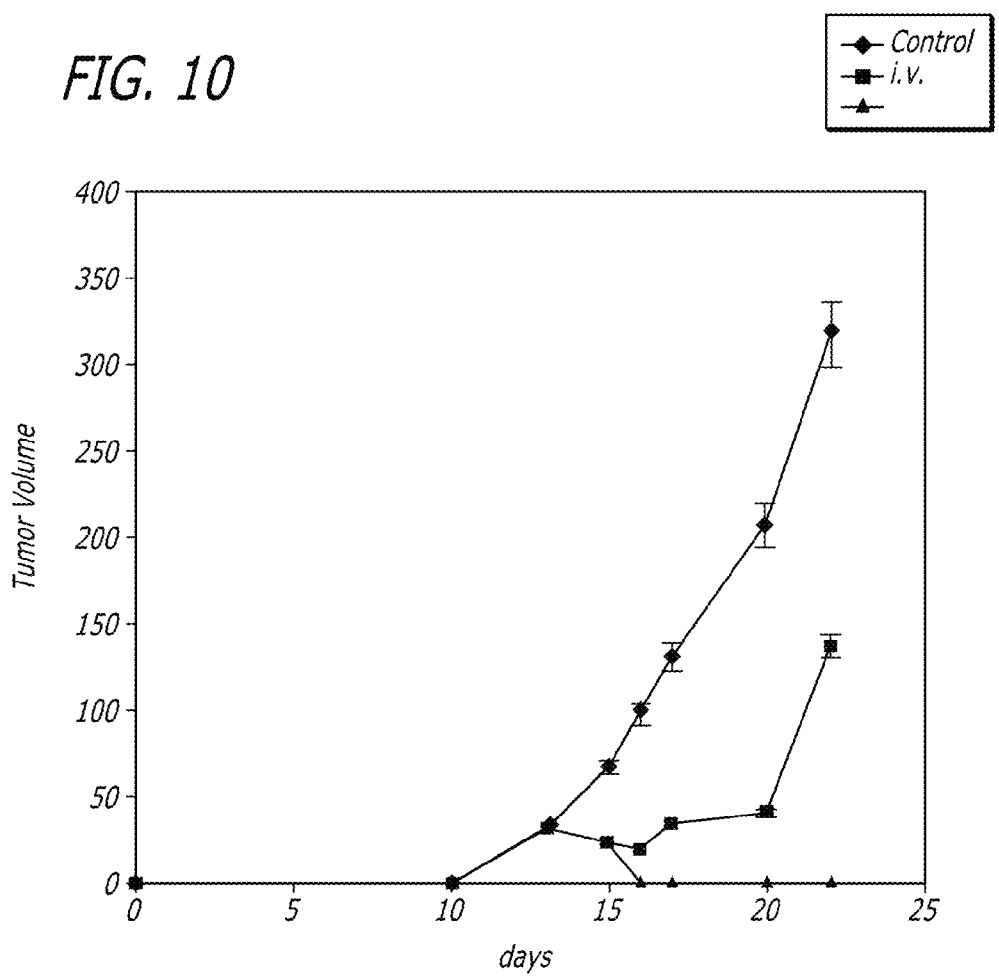
FIG. 10 depicts Nani-P2 treatment-induced regression of established 4T1 breast tumors. One of 10 mice underwent a complete remission and remained disease-free over 50 days, at which point the study was terminated. Two groups of 10 BALB/c mice were injected with $1\times10^4$ 4T1 cells in the mammary pad on day 0. One group was dosed with Nani-P2 (40 ng) per mouse IV weekly over three weeks beginning at day 14 and the other group was treated with PBS and served as control. The difference in primary tumor growth between control and Nani-P2-treated groups was highly significant (p<0.01**).

Nani-P2 efficacy in the setting of pre-established, aggressive 4T1 breast cancer is clearly and significantly proven by comparing primary tumor burden in intravenously-treated animals (40 ng IV Nani-P2) against control (PBS-treated) animals (at day 18 p<0.01, FIG. 10). This statistically significant benefit in primary tumor suppression (FIG. 10) remained throughout the duration of the trial lasting 50 days (p<0.01) even though only three weekly doses of PINS were administered between days 14 and 28. Moreover 7/10 mice demonstrated regression of tumor at the initial treatment of tumor on day 14. This translated into a very highly statistically significant benefit to survival (p<0.005**, and see FIG. 5B). Remarkably 1/10 animals underwent a complete remission and remained disease-free at 50 days at which point the study was terminated, supporting the inference that this animal had been rendered apparently tumor-free.

EXAMPLE 4

Repeated Dosing Therapy of Tat Derivatives and Cyclophosphamide

Four groups of 10 BALB/c mice were implanted with $1 \times 10^4$ 4T1 cells SC into the mammary fat pad. Treatment was initiated when tumor diameters reached 4-5 mm, on day 10. Control mice were injected IV with PBS at 3 days intervals, while alternating treatment mice received 3 doses of drug every 3 days in rotating 10 day cycles. Tumor burden (tumor size $mm^3$) was calculated using a standard formula. CY: (cyclophosphamide alone) mice were injected IP weekly with 80 mg/kg per mouse beginning on day 10. Cy/Nani-P2: (cyclophosphamide first followed by Nani-P2) mice were first injected IP with cyclophosphamide (80 mg/kg) at 3 days intervals for three doses starting at day 10 and then injected IV with Nani-P2 (40 ng) at 3 days intervals for three doses in rotation. The cycle of 3 doses of CY followed by 3 doses of Nani-P2 was repeated until day 50. Nani-P2/CY: (Nani-P2 first followed by cyclophosphamide): mice were first injected IV with Nani-P2 (40 ng) at 3 day intervals for 3 doses starting on day 10 and then injected i.p. with cyclophosphamide at 3 day intervals in rotation. The cycle of 3 doses of Nani-P2 followed by 3 doses of CY was repeated until day 50.

Figure 11:
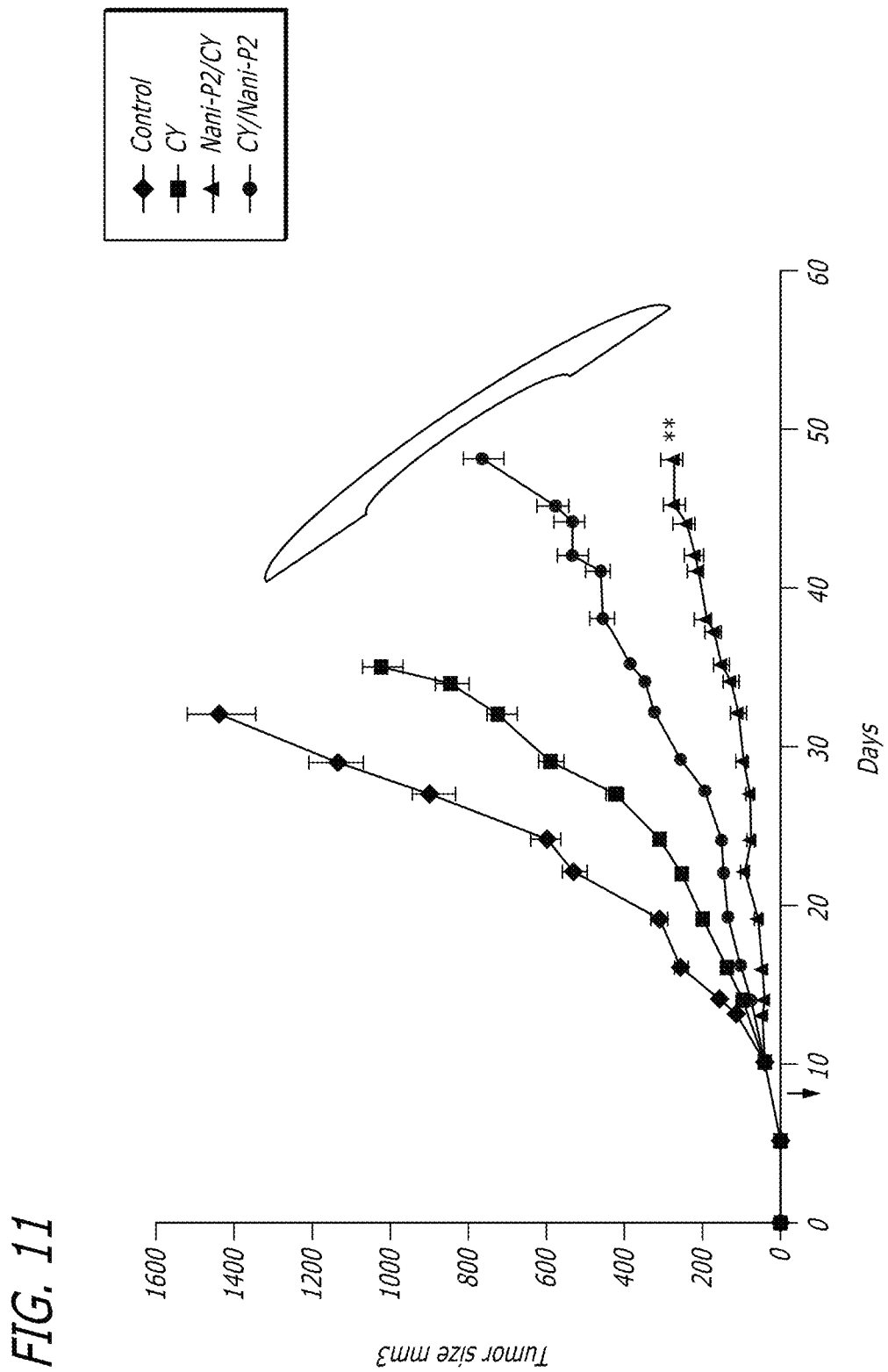
FIG. 11 depicts tumor growth after therapy with repeated doses of Nani-P2 and cyclophosphamide.

The decreased tumor burden in the Nani-P2/CY group compared to the CY group is very highly statistically significant (FIG. 11, p=0.003077).

Figure 12:
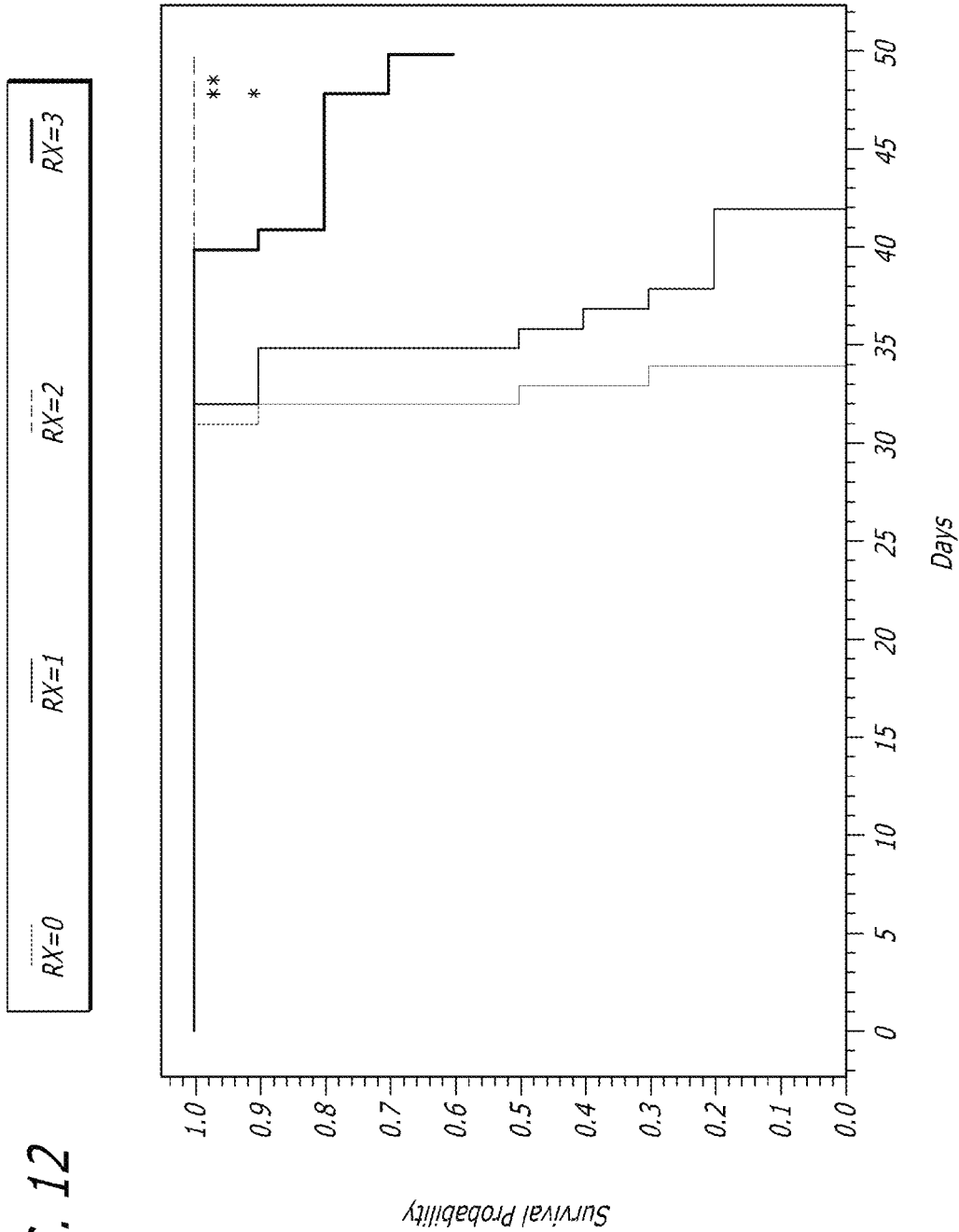
FIG. 12 depicts the survival benefit of repeated doses of Nani-P2 and cyclophosphamide vs. weekly cyclophosphamide.

The survival benefit of Nani-P2 bolus treatment alternating with cyclophosphamide vs. weekly cyclophosphamide is highly statistically significant (FIG. 12, p=0.0001). The Nani- P2 cohort has 3/10 mice in total remission and 9/10 mice in partial remission at day 50 (not shown), while 10/10 cyclophosphamide treated mice were dead by day 42.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A pharmaceutical composition comprising a modified amino acid sequence of Human Immunodeficiency Virus (HIV) trans-activator of transcription (Tat) protein wherein the modified amino acid sequence has greater than 95% sequence identity to the amino acid sequence of SEQ ID NO:2 or SEQ ID NO:3.

2. The pharmaceutical composition of claim 1, wherein the modified amino acid sequence has greater than 95% sequence identity to the amino acid sequence of SEQ ID NO:2.

3. The pharmaceutical composition of claim 1, wherein the modified amino acid sequence has greater than 95% sequence identity to the amino acid sequence of SEQ ID NO:3.

4. A method of treating breast or ovarian cancer comprising:

administering a therapeutically effective amount of a Tat derivative polypeptide comprising the modified amino acid sequence of claim 1 to a subject in need thereof; and causing cessation of growth of the cancer or regression of the cancer in the subject.

5. The method of claim 4, wherein the Tat derivative polypeptide is administered in a plurality of doses.

6. The method of claim 4, wherein the administering step comprises a repetitive administration cycle wherein each cycle comprises administering a plurality of doses of the Tat derivative polypeptide in a defined time period followed by a rest period and wherein the cycle is repeated a plurality of times.

7. The method of claim 4, wherein the administering step comprises a repetitive administration cycle wherein each cycle comprises administering a plurality of doses of the Tat derivative polypeptide in a defined time period followed by a administration of one or a plurality of doses of a therapeutic agent in a defined time period and wherein the cycle is repeated a plurality of times.

8. The method of claim 7, wherein the therapeutic agent is cyclophosphamide.

9. The method of claim 7, wherein the cancer is breast cancer.

10. The method of claim 7, wherein the cancer is ovarian cancer.

11. The method of claim 4, wherein the Tat derivative polypeptide comprises a modified amino acid sequence having greater than 95% sequence identity to the amino acid sequence of SEQ ID NO:2.

12. The method of claim 4, wherein the Tat derivative polypeptide comprises a modified amino acid sequence having greater than 95% sequence identity to the amino acid sequence of SEQ ID NO:3.

13. A method of reducing breast cancer tumor burden or ovarian cancer tumor burden comprising:

administering a therapeutically effective amount of the a Tat derivative polypeptide comprising the modified amino acid sequence of claim 1 to a subject in need thereof; and causing regression of the cancer in the subject.

14. The method of claim 13, wherein the Tat derivative polypeptide is administered in a plurality of doses.

15. The method of claim 13, wherein the administering step comprises a repetitive administration cycle wherein each cycle comprises administering a plurality of doses of the Tat derivative polypeptide in a defined time period followed by a rest period and wherein the cycle is repeated a plurality of times.

16. The method of claim 13, wherein the administering step comprises a repetitive administration cycle wherein each cycle comprises administering a plurality of doses of the Tat derivative polypeptide in a defined time period followed by an administration of one or a plurality of doses of a therapeutic agent in a defined time period and wherein the cycle is repeated a plurality of times.

17. The method of claim 16, wherein the therapeutic agent is cyclophosphamide.

18. The method of claim 13, wherein the cancer is breast cancer.

19. The method of claim 13, wherein the cancer is ovarian cancer.

* * * * *